United States Patent
Vivenzio et al.

(10) Patent No.: US 8,388,523 B2
(45) Date of Patent: Mar. 5, 2013

(54) MEDICAL DIAGNOSTIC INSTRUMENT HAVING PORTABLE ILLUMINATOR

(75) Inventors: Robert L. Vivenzio, Auburn, NY (US); Raymond A. Lia, Auburn, NY (US); Ian K. Edwards, Skaneateles, NY (US); Thaddeus Wawro, Auburn, NY (US); Steven R. Slawson, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 885 days.

(21) Appl. No.: 12/477,662

(22) Filed: Jun. 3, 2009

(65) Prior Publication Data
US 2009/0287192 A1 Nov. 19, 2009

Related U.S. Application Data

(63) Continuation-in-part of application No. 11/910,387, filed as application No. PCT/US2006/012116 on Apr. 3, 2006, and a continuation-in-part of application No. 11/910,378, filed as application No. PCT/US2006/012320 on Apr. 3, 2006, now Pat. No.
(Continued)

(51) Int. Cl.
*A61B 1/06* (2006.01)
*A61B 1/227* (2006.01)

(52) U.S. Cl. ........ 600/178; 600/131; 600/199; 600/200; 362/574

(58) Field of Classification Search .......... 600/131, 600/178, 179, 199, 200, 223, 249; 362/154, 362/155, 109, 572, 574
See application file for complete search history.

(56) References Cited

U.S. PATENT DOCUMENTS

| | | | |
|---|---|---|---|
| 553,728 A | 1/1896 | Campbell | |
| 2,039,546 A * | 5/1936 | McGerry | 600/200 |
| 2,235,979 A * | 3/1941 | Brown | 600/178 |
| 3,592,199 A * | 7/1971 | Ostensen | 600/198 |
| 3,716,047 A | 2/1973 | Moore et al. | |
| 3,766,909 A * | 10/1973 | Ozbey | 600/193 |
| 3,789,835 A | 2/1974 | Whitman | |
| 3,885,211 A | 5/1975 | Gutai | |
| 3,934,578 A * | 1/1976 | Heine | 600/200 |
| 3,945,371 A | 3/1976 | Adelman | |

(Continued)

FOREIGN PATENT DOCUMENTS

| | | |
|---|---|---|
| CN | 2053088 U | 2/1990 |
| CN | 2387854 Y | 7/2000 |

(Continued)

OTHER PUBLICATIONS

International Search Report and Written Opinion for PCT/US2009/046207, mailed Jan. 8, 2010 (10 pages).

(Continued)

*Primary Examiner* — John P Leubecker

(57) ABSTRACT

A portable medical diagnostic instrument includes an instrument head and a handle portion having an open-ended receiving cavity. A compact illuminator defined by a housing retaining a miniature light source and a power supply is releasably fitted within the open-ended receiving cavity of the handle portion wherein the light source of the illuminator is optically coupled with the instrument on assembly therewith. The handle portion can be integral with the instrument or releasably attached. The handle portion according to at least one version is made from a plastic or other suitable material, permitting disposability and/or single patient use. In one version, the handle portion is flexibly deformable, at least partially, to facilitate release of the portable illuminator.

28 Claims, 24 Drawing Sheets

Related U.S. Application Data 8,157,728, and a continuation-in-part of application No. 11/910,399, filed as application No. PCT/US2006/012322 on Apr. 3, 2006, now abandoned.

(60) Provisional application No. 61/130,951, filed on Jun. 4, 2008, provisional application No. 60/735,576, filed on Nov. 10, 2005, provisional application No. 60/667,505, filed on Apr. 1, 2005.

U.S. PATENT DOCUMENTS

| Patent No. | Kind | Date | Name |
|---|---|---|---|
| 3,978,850 | A * | 9/1976 | Moore et al. .................. 600/200 |
| D245,515 | S | 8/1977 | Troutner et al. |
| 4,067,323 | A | 1/1978 | Troutner et al. |
| 4,156,424 | A | 5/1979 | Burgin |
| 4,210,133 | A | 7/1980 | Castaneda |
| 4,220,985 | A | 9/1980 | Hukuba |
| 4,227,537 | A | 10/1980 | Suciu et al. |
| 4,263,899 | A | 4/1981 | Burgin |
| 4,337,763 | A | 7/1982 | Petrassevich |
| 4,432,351 | A | 2/1984 | Hoary |
| 4,492,220 | A | 1/1985 | Hayes |
| 4,502,468 | A | 3/1985 | Burgin |
| 4,517,628 | A | 5/1985 | McDermott |
| 4,517,702 | A | 5/1985 | Jackson |
| 4,546,761 | A | 10/1985 | McCullough |
| 4,562,832 | A | 1/1986 | Wilder et al. |
| 4,566,439 | A | 1/1986 | Burgin |
| 4,567,881 | A | 2/1986 | Heller |
| 4,597,383 | A | 7/1986 | VanDerBel |
| 4,607,623 | A | 8/1986 | Bauman |
| 4,619,248 | A | 10/1986 | Walsh |
| 4,638,792 | A | 1/1987 | Burgin |
| 4,646,722 | A | 3/1987 | Silverstein et al. |
| 4,729,367 | A | 3/1988 | Bauman |
| 4,741,326 | A | 5/1988 | Sidall et al. |
| 4,763,678 | A | 8/1988 | Ott |
| 4,766,887 | A | 8/1988 | Cecil, Jr. et al. |
| 4,790,751 | A | 12/1988 | Reinhardt et al. |
| D299,532 | S | 1/1989 | Cecil, Jr. et al. |
| 4,807,600 | A | 2/1989 | Hayes |
| 4,811,937 | A | 3/1989 | Rothman |
| 4,823,244 | A * | 4/1989 | Alaybayoglu et al. ........ 362/194 |
| 4,825,850 | A | 5/1989 | Opie et al. |
| 4,869,238 | A | 9/1989 | Opie et al. |
| 4,872,837 | A | 10/1989 | Issalene et al. |
| 4,884,559 | A | 12/1989 | Collins |
| 4,971,036 | A | 11/1990 | Collins |
| 4,979,498 | A | 12/1990 | Oneda et al. |
| 4,981,086 | A | 1/1991 | Barca |
| 5,018,507 | A | 5/1991 | Montaldi |
| 5,026,368 | A | 6/1991 | Adair |
| 5,054,906 | A | 10/1991 | Lyons, Jr. |
| 5,063,908 | A | 11/1991 | Collins |
| 5,067,491 | A | 11/1991 | Taylor, II et al. |
| 5,143,054 | A | 9/1992 | Adair |
| RE34,110 | E | 10/1992 | Opie |
| 5,165,387 | A | 11/1992 | Woodson |
| 5,174,278 | A | 12/1992 | Babkow |
| 5,179,937 | A | 1/1993 | Lee |
| 5,179,938 | A | 1/1993 | Lonky |
| 5,201,908 | A | 4/1993 | Jones |
| 5,222,271 | A | 6/1993 | Eganhouse |
| 5,250,065 | A | 10/1993 | Clement et al. |
| 5,284,474 | A | 2/1994 | Adair |
| 5,306,237 | A | 4/1994 | Clement et al. |
| 5,329,938 | A | 7/1994 | Lonky |
| 5,337,734 | A | 8/1994 | Saab |
| 5,338,292 | A | 8/1994 | Clement et al. |
| 5,349,941 | A | 9/1994 | Hori |
| 5,374,244 | A | 12/1994 | Clement et al. |
| 5,386,817 | A | 2/1995 | Jones |
| 5,394,863 | A | 3/1995 | Sanford et al. |
| 5,458,132 | A | 10/1995 | Yabe et al. |
| 5,465,709 | A | 11/1995 | Dickie et al. |
| 5,499,964 | A * | 3/1996 | Beck et al. .................... 600/220 |
| 5,588,950 | A | 12/1996 | Sano et al. |
| 5,595,344 | A | 1/1997 | Starnes |
| 5,639,238 | A | 6/1997 | Fishburne, Jr. |
| 5,656,014 | A | 8/1997 | Rooney et al. |
| 5,695,492 | A | 12/1997 | Brown |
| 5,699,794 | A | 12/1997 | Fleck |
| 5,711,921 | A | 1/1998 | Langford |
| 5,716,329 | A | 2/1998 | Dieter |
| 5,746,694 | A | 5/1998 | Wilk |
| 5,772,435 | A | 6/1998 | Dorman |
| 5,772,581 | A * | 6/1998 | Gaines .......................... 600/190 |
| 5,785,648 | A | 7/1998 | Min |
| 5,836,764 | A | 11/1998 | Buchanan |
| 5,846,249 | A | 12/1998 | Thompson |
| 5,865,729 | A | 2/1999 | Meehan et al. |
| 5,873,820 | A | 2/1999 | Norell |
| 5,879,286 | A | 3/1999 | Krauter et al. |
| 5,899,854 | A | 5/1999 | Slishman |
| 5,906,802 | A | 5/1999 | Langford |
| 5,916,150 | A | 6/1999 | Sillman |
| 5,916,151 | A | 6/1999 | Charters |
| 5,921,777 | A | 7/1999 | Dorman |
| 5,934,904 | A | 8/1999 | Elrod et al. |
| 5,941,834 | A | 8/1999 | Skladnev et al. |
| 5,961,937 | A | 10/1999 | Gobbato |
| 6,004,265 | A | 12/1999 | Hsu et al. |
| 6,030,210 | A | 2/2000 | Bianchetti |
| 6,036,638 | A | 3/2000 | Nwanka |
| 6,048,308 | A | 4/2000 | Strong |
| 6,083,151 | A * | 7/2000 | Renner et al. ................. 600/114 |
| 6,095,810 | A | 8/2000 | Bianchetti |
| 6,102,851 | A * | 8/2000 | Mellin .......................... 600/199 |
| 6,117,285 | A | 9/2000 | Welch et al. |
| 6,130,520 | A | 10/2000 | Wawro et al. |
| 6,159,162 | A | 12/2000 | Kostylev et al. |
| 6,176,824 | B1 | 1/2001 | Davis |
| 6,179,614 | B1 | 1/2001 | Elrod et al. |
| 6,186,944 | B1 | 2/2001 | Tsai |
| 6,217,512 | B1 | 4/2001 | Salo et al. |
| 6,277,067 | B1 | 8/2001 | Blair |
| 6,319,199 | B1 | 11/2001 | Sheehan et al. |
| 6,346,085 | B1 | 2/2002 | Schiffman |
| 6,361,489 | B1 | 3/2002 | Tsai |
| 6,379,296 | B1 | 4/2002 | Baggett |
| 6,379,299 | B1 | 4/2002 | Borodulin et al. |
| 6,394,111 | B1 | 5/2002 | Jacobs et al. |
| 6,394,950 | B1 | 5/2002 | Weiss |
| 6,397,847 | B1 | 6/2002 | Scarberry et al. |
| 6,432,045 | B2 | 8/2002 | Lemperle |
| 6,432,049 | B1 | 8/2002 | Banta et al. |
| 6,436,033 | B2 | 8/2002 | Tan |
| 6,450,952 | B1 | 9/2002 | Rioux et al. |
| 6,454,874 | B1 | 9/2002 | Jacobs et al. |
| 6,468,232 | B1 | 10/2002 | Ashton-Miller et al. |
| 6,487,440 | B2 | 11/2002 | Deckert et al. |
| 6,494,964 | B1 | 12/2002 | Jacobs et al. |
| 6,514,198 | B2 | 2/2003 | Ishibiki |
| 6,516,817 | B2 | 2/2003 | Jacobs |
| 6,516,818 | B2 | 2/2003 | Jacobs |
| 6,524,259 | B2 | 2/2003 | Baxter-Jones et al. |
| 6,569,091 | B2 | 5/2003 | Diokno et al. |
| 6,585,727 | B1 | 7/2003 | Cashman et al. |
| 6,589,168 | B2 | 7/2003 | Thompson |
| 6,595,917 | B2 | 7/2003 | Nieto |
| 6,610,020 | B2 | 8/2003 | Voegele |
| 6,626,825 | B2 | 9/2003 | Tsai |
| 6,663,576 | B2 | 12/2003 | Gombrich et al. |
| 6,731,961 | B2 | 5/2004 | Braig et al. |
| 6,739,744 | B2 | 5/2004 | Williams et al. |
| 6,743,198 | B1 | 6/2004 | Tihon |
| 6,761,687 | B1 | 7/2004 | Doshi et al. |
| 6,830,547 | B2 | 12/2004 | Weiss |
| 6,847,490 | B1 | 1/2005 | Nordstrom et al. |
| 6,875,169 | B2 * | 4/2005 | Berci et al. .................... 600/112 |
| 6,889,832 | B2 | 5/2005 | Gabele |
| 6,895,965 | B2 | 5/2005 | Scarberry et al. |
| 6,896,653 | B1 | 5/2005 | Vail, III |
| 6,908,428 | B2 | 6/2005 | Aizenfeld et al. |
| 6,929,601 | B2 | 8/2005 | Nakao |
| 6,957,897 | B1 | 10/2005 | Nelson et al. |

| | | |
|---|---|---|
| 6,974,294 B2 | 12/2005 | Pressman |
| 7,014,340 B2 | 3/2006 | Bettis |
| 7,018,592 B2 | 3/2006 | Bowen |
| 7,021,798 B2 | 4/2006 | Tsimerman |
| 7,060,039 B2 | 6/2006 | Voegele |
| 7,909,759 B2 * | 3/2011 | Pecherer ................. 600/193 |
| 2001/0029044 A1 | 10/2001 | Gombrich et al. |
| 2001/0029387 A1 | 10/2001 | Wolf et al. |
| 2001/0033805 A1 | 10/2001 | Jacobs et al. |
| 2001/0034917 A1 | 11/2001 | DuCey |
| 2002/0016525 A1 | 2/2002 | Ishibiki |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0058230 A1 | 5/2002 | Savin et al. |
| 2002/0119419 A1 | 8/2002 | Suzuki et al. |
| 2002/0120210 A1 | 8/2002 | Voegele |
| 2002/0137006 A1 | 9/2002 | Gugel et al. |
| 2002/0137008 A1 | 9/2002 | McSpadden et al. |
| 2002/0156350 A1 | 10/2002 | Nieto |
| 2002/0156395 A1 | 10/2002 | Stephens et al. |
| 2002/0162304 A1 | 11/2002 | Stravitz |
| 2002/0165433 A1 | 11/2002 | Stihl |
| 2002/0165435 A1 | 11/2002 | Weiss |
| 2002/0170133 A1 | 11/2002 | McDevitt et al. |
| 2002/0198471 A1 | 12/2002 | Baxter-Jones et al. |
| 2003/0079654 A1 * | 5/2003 | Tokiwa et al. ............. 106/162.7 |
| 2003/0083547 A1 | 5/2003 | Hamilton et al. |
| 2003/0114803 A1 | 6/2003 | Lerner |
| 2003/0125666 A1 | 7/2003 | Kasahara et al. |
| 2003/0134255 A1 | 7/2003 | Masterman et al. |
| 2003/0139673 A1 | 7/2003 | Vivenzio et al. |
| 2003/0158502 A1 | 8/2003 | Baxter-Jones et al. |
| 2003/0164182 A1 | 9/2003 | Jacobs et al. |
| 2003/0176772 A1 | 9/2003 | Yang |
| 2003/0187331 A1 | 10/2003 | Faludi et al. |
| 2003/0188761 A1 | 10/2003 | Garcia et al. |
| 2003/0195434 A1 | 10/2003 | Voegele |
| 2003/0208995 A1 | 11/2003 | Stravitz |
| 2003/0213074 A1 | 11/2003 | Kawazoe et al. |
| 2003/0213082 A1 | 11/2003 | Tanaka |
| 2004/0014000 A1 | 1/2004 | Bernhard |
| 2004/0026829 A1 | 2/2004 | Van Der Weegen |
| 2004/0059253 A1 | 3/2004 | Martone et al. |
| 2004/0076019 A1 | 4/2004 | Tsimerman et al. |
| 2004/0083681 A1 | 5/2004 | Stravitz |
| 2004/0084058 A1 | 5/2004 | Tyndai |
| 2004/0084070 A1 | 5/2004 | Sasaki et al. |
| 2004/0118440 A1 | 6/2004 | Sasaki et al. |
| 2004/0141175 A1 | 7/2004 | Baldwin et al. |
| 2004/0166474 A1 | 8/2004 | Gugel et al. |
| 2004/0183482 A1 | 9/2004 | Roberts et al. |
| 2004/0184288 A1 * | 9/2004 | Bettis ........................ 362/572 |
| 2004/0186352 A1 | 9/2004 | Roberts et al. |
| 2004/0186355 A1 | 9/2004 | Strong et al. |
| 2004/0190140 A1 | 9/2004 | Bala |
| 2004/0191723 A1 | 9/2004 | Shearer et al. |
| 2004/0210114 A1 | 10/2004 | Simon |
| 2004/0225267 A1 | 11/2004 | Tapadiya |
| 2005/0017078 A1 * | 1/2005 | Bhatia et al. ............. 235/462.45 |
| 2005/0021017 A1 | 1/2005 | Karasawa et al. |
| 2005/0033119 A1 | 2/2005 | Okawa et al. |
| 2005/0054894 A1 | 3/2005 | Aizenfeld et al. |
| 2005/0065496 A1 | 3/2005 | Simon |
| 2005/0071938 A1 | 4/2005 | McDevitt et al. |
| 2005/0073244 A1 | 4/2005 | Chou et al. |
| 2005/0080462 A1 | 4/2005 | Jenkins et al. |
| 2005/0085699 A1 | 4/2005 | Weiss |
| 2005/0125027 A1 | 6/2005 | Knodel et al. |
| 2005/0137613 A1 | 6/2005 | Kasahara et al. |
| 2005/0148819 A1 | 7/2005 | Noguchi et al. |
| 2005/0159752 A1 | 7/2005 | Walker et al. |
| 2005/0161586 A1 | 7/2005 | Rains et al. |
| 2005/0162028 A1 | 7/2005 | Kardeis et al. |
| 2005/0192482 A1 | 9/2005 | Carpenter et al. |
| 2005/0209507 A1 | 9/2005 | Suzuki et al. |
| 2005/0214881 A1 | 9/2005 | Azarnia et al. |
| 2005/0215858 A1 | 9/2005 | Vail, III |
| 2005/0222601 A1 | 10/2005 | Erhard |
| 2005/0236230 A1 | 10/2005 | Fee |
| 2005/0261763 A1 | 11/2005 | Wang |
| 2005/0274093 A1 | 12/2005 | Stravitz et al. |
| 2005/0278020 A1 | 12/2005 | Wang |
| 2005/0282112 A1 | 12/2005 | Kumar |
| 2005/0286130 A1 | 12/2005 | Bala |
| 2006/0004271 A1 | 1/2006 | Peyser et al. |
| 2006/0027246 A1 | 2/2006 | Wilkinson |
| 2006/0029901 A1 | 2/2006 | Rose et al. |
| 2006/0037165 A1 | 2/2006 | McDevitt et al. |
| 2006/0041274 A1 | 2/2006 | Su |
| 2006/0046226 A1 | 3/2006 | Bergler et al. |
| 2006/0084843 A1 | 4/2006 | Sommerich et al. |
| 2006/0085932 A1 | 4/2006 | Santos |
| 2006/0089529 A1 | 4/2006 | Tartaglia et al. |
| 2006/0104856 A1 | 5/2006 | Farrell |
| 2006/0110700 A1 | 5/2006 | Cipolla et al. |
| 2006/0116551 A1 | 6/2006 | Lovett et al. |
| 2006/0127844 A1 | 6/2006 | Michaelian |
| 2006/0130438 A1 | 6/2006 | Stravitz et al. |
| 2006/0137122 A1 | 6/2006 | Ryan |
| 2006/0155169 A1 * | 7/2006 | Bastia et al. ................. 600/199 |
| 2007/0230164 A1 * | 10/2007 | Vivenzio et al. .............. 362/109 |
| 2007/0230167 A1 * | 10/2007 | McMahon et al. ............ 362/157 |
| 2008/0045801 A1 * | 2/2008 | Shalman et al. ............. 600/193 |
| 2008/0200766 A1 * | 8/2008 | Ayoun et al. ................. 600/199 |
| 2010/0022843 A1 * | 1/2010 | Pecherer et al. ............. 600/197 |

FOREIGN PATENT DOCUMENTS

| | | |
|---|---|---|
| GB | 553 728 | 6/1943 |
| WO | WO2004037287 A2 | 5/2004 |
| WO | WO 2006050574 | 5/2006 |
| WO | WO 2006121530 | 11/2006 |

OTHER PUBLICATIONS

European Office Action for EP Application No. 06 749 170.4; dated Jan. 17, 2011; 4 pages.
Supplementary European Search Report for EP Application No. 06 769 794.6; mailed May 8, 2009; 9 pages.
Supplementary European Search Report for EP Application No. 06 749 169.6; mailed May 8, 2009; 9 pages.
Supplementary European Search Report for EP Application No. 06 749 170.4; mailed May 8, 2009; 13 pages.
International Search Report/Written Opinion for PCT/US2007/088514 (ISR/WO); mailed Jun. 5, 2008; 7 pages.
International Search Report/Written Opinion for PCT/US2006/012320 (ISR/WO); mailed Sep. 26, 2007; 4 pages.
International Search Report/Written Opinion for PCT/US2006/012116 (ISR/WO); mailed May 29, 2007; 5 pages.
International Search Report/Written Opinion for PCT/US2006/012322 (ISR/WO); mailed May 29, 2007; 6 pages.

* cited by examiner

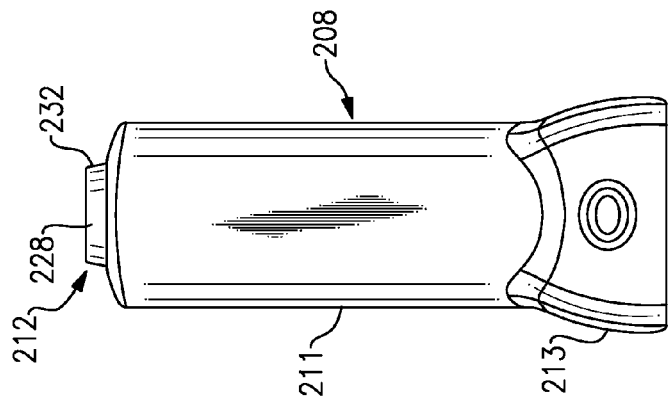
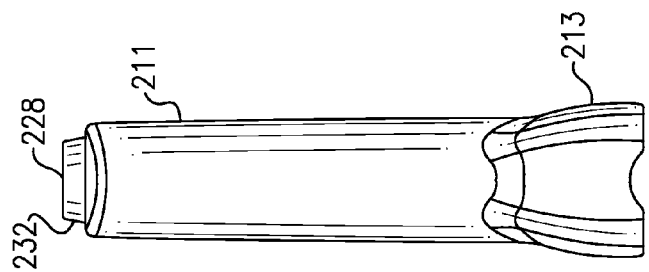
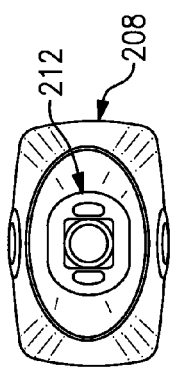
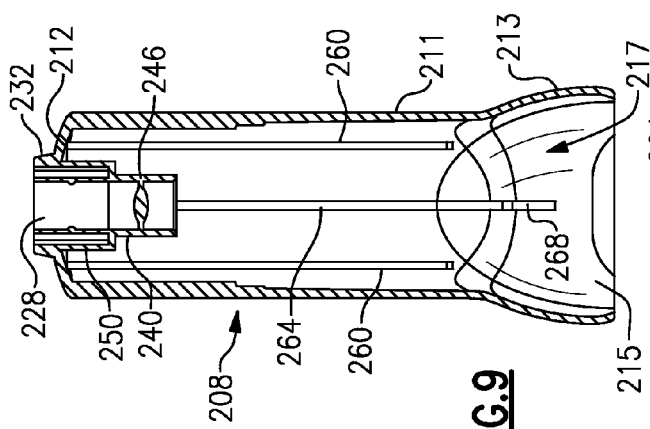
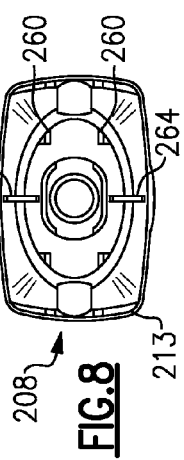

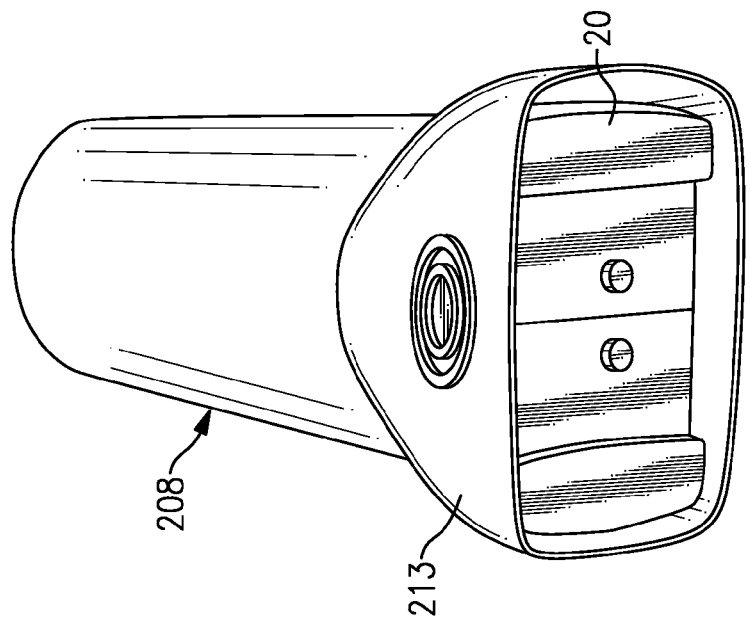
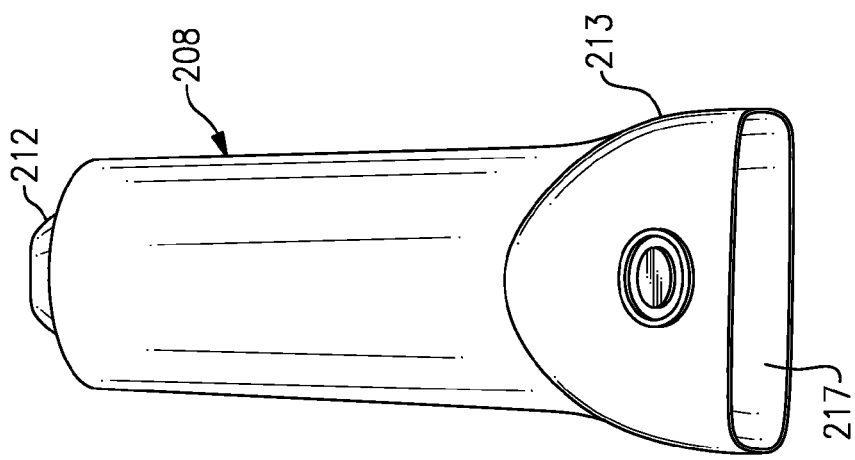
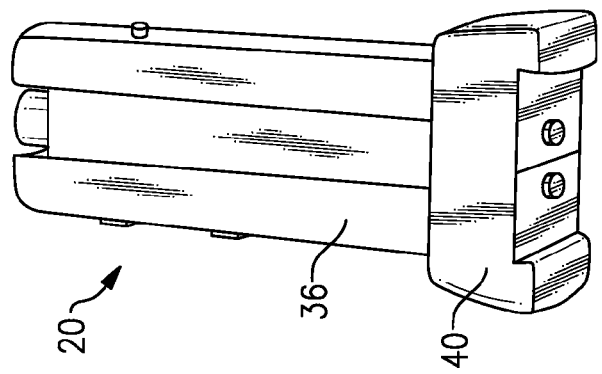
FIG.12(a)
FIG.12(b)

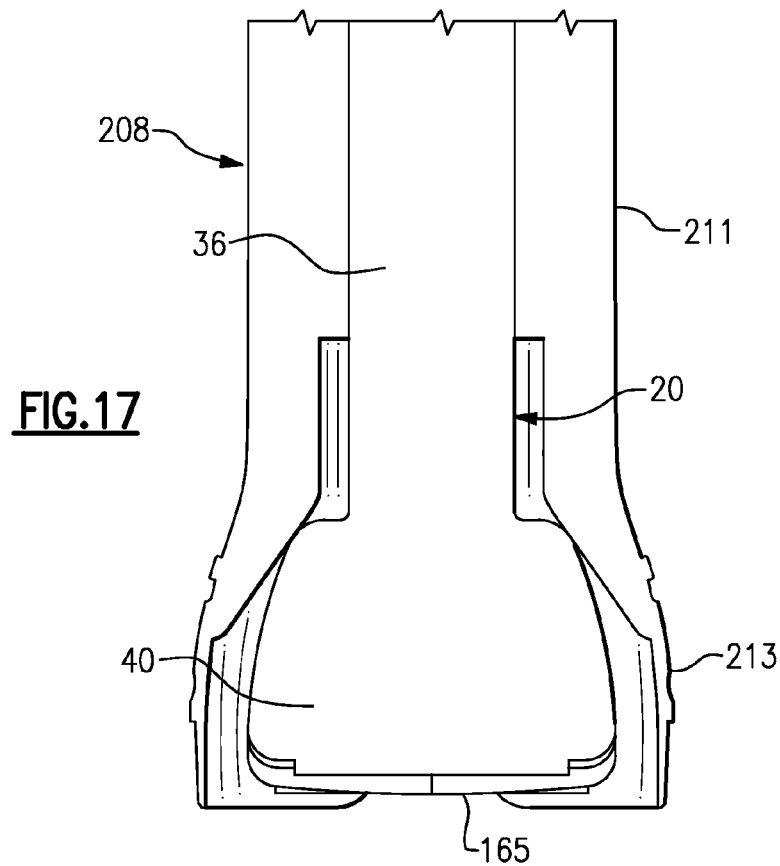
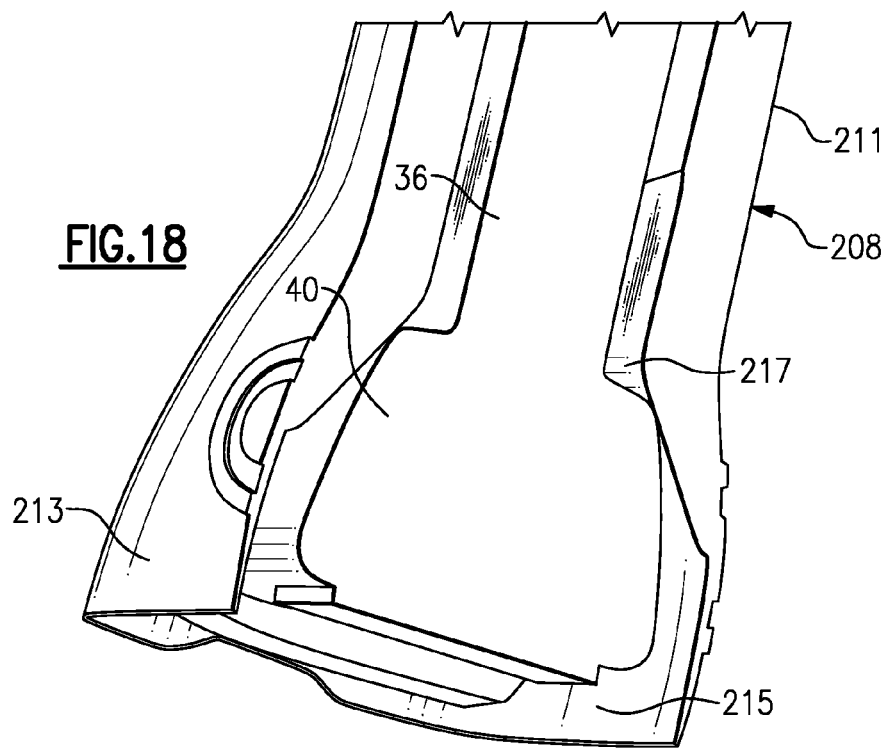

MEDICAL DIAGNOSTIC INSTRUMENT HAVING PORTABLE ILLUMINATOR

CROSS REFERENCE TO RELATED APPLICATIONS

This patent application claims priority upon a provisional application, U.S. Ser. No. 61/130,951, filed Jun. 4, 2008, pursuant to 35 USC §119(e). This application is a continuation-in-part (CIP) of the following corresponding United States applications pursuant to 35 USC §120; namely, U.S. Ser. No. 11/910,387, filed Apr. 25, 2008, which is a national stage application of PCT/US2006/012116, filed Apr. 3, 2006, which claims benefit of U.S. Ser. No. 60/735,576, filed Nov. 10, 2005 and U.S. Ser. No. 60/667,505, filed Apr. 1, 2005; U.S. Ser. No. 11/910,378, filed Apr. 25, 2008 (U.S. Pat. No. 8,157,728), which is a national stage application of PCT/US2006/012320, filed Apr. 3, 2006, which claims benefit of U.S. Ser. No. 60/735,576, filed Nov. 10, 2005 and U.S. Ser. No. 60/667,505, filed Apr. 1, 2005; and U.S. Ser. No. 11/910,399, filed May 7, 2008 (abandoned), which is a national stage application of PCT/US2006/012322, filed Apr. 3, 2006, which claims benefit of U.S. Ser. No. 60/735,576, filed Nov. 10, 2005 and U.S. Ser. No. 60/667,505, filed Apr. 1, 2005, the entire contents of each above-noted application being incorporated by reference herein.

FIELD OF THE INVENTION

The application relates to the field of diagnostic medicine and more particularly to various medical instruments that is configured to releasably support a portable illuminator so as to prevent cross-contamination between patients and in which the supported illuminator is releasably retained within the handle of the instrument and optically coupled with the instrument. In one version, the portable illuminator can be used interchangeably with a plurality of various hand-held medical diagnostic instruments.

BACKGROUND OF THE INVENTION

Applicant has previously developed a portable illumination assembly for use with vaginal specula, as described in International Publication Number WO 2006/121530A2. Prior to development of this assembly, tethered or corded illumination assemblies were required in order to effectively conduct patent examinations in conjunction with vaginal specula. The use of corded illumination assemblies, however, introduced issues relating to contamination, versatility and ease of use. The portable illumination assembly, according to the above-noted '530 publication, includes a resident power supply and a compact light source that are each integrated within a single housing, wherein the illumination assembly can be positioned at least partially within the elongated cavity of a vaginal speculum handle. When positioned within the cavity of the speculum handle, the illumination assembly optically couples with the proximal end of a light pipe that is formed in the upper portion of the cavity of the speculum handle. The light pipe is defined by a distal light-emitting end that directs sufficient light from the attached illuminator to a medical target (e.g., the cervix of the patient).

It has since been considered adding the above-noted illumination assembly to other hand-held medical diagnostic instruments in an effort to better facilitate examination of patients using such instruments, to improve versatility and ease of use of these instruments, as well as to standardize a family or group of instruments in terms of their consistency and construction. That is to say, most types of hand-held diagnostic instruments (e.g., ophthalmoscopes, otoscopes, anoscopes, sigmoidscopes, among others) utilize different forms of power sources and illumination assemblies that are more or less dedicated to the specific instrument. One aim is to standardize such use, thereby significantly increasing versatility while also providing an improved illuminator to facilitate visualization of an examination area by supplying brighter, whiter light to the patient.

It is further desired to improve ease of use of hand-held medical diagnostic instruments, while also solving issues such as cross contamination in the use thereof. In the use of tethered illumination assemblies, for example, a highly flexible disposable protective sheath or covering is required to prevent patient cross contamination with regard to the portion of the assembly and cord extending from the diagnostic instrument. Though effective in terms of this aim, there are subsidiary issues relating to having to provide an on-hand inventory of sheath members, as well as waste disposal and environmental concerns. Therefore, it is a general desire in the field to substantially minimize cross contamination of such assemblies to enable re-use of an illumination assembly between patients, but without requiring a separate sheath or covering.

SUMMARY OF THE INVENTION

Therefore and according to one aspect, there is provided a hand-held medical diagnostic instrument assembly, the assembly comprising a hand-held medical diagnostic instrument, the instrument including an instrument head and a handle portion. The handle portion includes an open-ended receiving cavity. The compact illuminator has a compact light source and a power supply each disposed within a housing. The illuminator is sized to fit substantially within the receiving cavity in releasable fashion, the handle portion further including means for optically coupling the light source of a retained illuminator with the instrument head. The optical coupling means includes a surface formed at a top of the receiving cavity bridging said handle portion and the interior of said instrument head, wherein the surface provides a fluid seal relative to the interior of said instrument head, and wherein the surface further having optical quality to enable the light source of the compact illuminator to be coupled to the instrument head when the illuminator is assembled within the handle portion.

According to one version, the handle portion is releasably attached to said instrument head. According to another version, the handle portion is integral to the instrument.

In one embodiment in which the handle portion is releasably attached, the handle portion is releasably attachable in multiple axial orientations relative to the instrument head. The open-ended receiving cavity in one version includes at least one guide rail, the at least one guide rail including a ramped surface within the deformable portion of the handle portion for engaging the compact illuminator when deformed to facilitate release of the illuminator.

The receiving cavity can also include at least one heat dissipating rib. The at least one heat dissipating rib also can serve as guide rails in said receiving cavity for the compact illuminator.

The optical coupling means can include a socket defined at the top of the handle portion, the socket including the surface. In one version, the surface is configured to have optical power. The socket can include means for guiding the portable illuminator into alignment with said surface when said illuminator is inserted into the receiving cavity. The socket enables the handle portion to be releasably attachable to the instrument head.

The handle portion can include at least one retaining feature for retaining said illuminator in said receiving cavity. In one version, the handle portion further includes at least one feature for facilitating release of the portable illuminator from the handle portion. According to one embodiment, at least a portion of said handle portion can be flexibly deformable.

The medical diagnostic instrument is preferably from at least one of the group consisting of a sigmoidoscope, an anoscope, an ophthalmoscope and an otoscope.

The handle portion is manufactured from a plastic material, wherein the handle portion can be disposable and moreover in which the handle portion is biodegradable or treated with an additive that renders the handle portion biodegradable.

The portable illuminator according to one version is automatically energized when said compact illuminator is inserted in said receiving cavity. The portable illuminator can be automatically deenergized when the illuminator is removed from the receiving cavity.

In yet another version a handle portion for a medical diagnostic instrument is provided, the handle portion including a housing having an open-ended receiving cavity that is sized to receive a portable illuminator. The handle portion is releasably couplable to the body of the medical diagnostic instrument wherein in which at least a portion of the handle portion is flexibly deformable.

According to yet another aspect, there is provided a diagnostic instrument system that comprises a plurality of hand-held medical diagnostic instruments, each of the diagnostic instruments including a handle portion having an open-ended receiving cavity and an instrument head, and a portable illuminator separably and releasably couplable within the open-ended receiving cavity of each of the hand-held diagnostic instruments. Each said handle portion includes means for optically coupling the portable illuminator with the instrument head to deliver light to a medical target.

One advantage of the herein described assembly is greater degree of user versatility achieved by providing at least one medical diagnostic instrument that releasably accepts a portable illuminator. Another advantage provided is greater ease of use of hand-held diagnostic instruments so equipped. Yet another advantage is the ability to develop disposable component(s) to prevent cross contamination during procedures and thereby substantially eliminate time and expense of reprocessing and cleaning.

Another advantage is that instruments so configured can be provided with improved and consistent ergonomics, enabling better "feel" for the user. Yet another advantage is that portability of a common illuminator enables selectivity of light sources, such as LEDs, providing greater selectivity between different color temperatures and therefore affording choices as to illumination sources and enabling improvements to be added simultaneously to a family of instruments. As such, improved visualization of an examination area is possible by supplying whiter, brighter light. Yet another advantage is that the handle portion can be made disposable, but without creating environmental issues.

These and other features and advantages will become readily apparent from the following Detailed Description, which should be read in conjunction with the accompanying drawings.

BRIEF DESCRIPTION OF THE DRAWINGS

FIG. 7 is a top plan view of a handle portion for use with the medical diagnostic instrument of FIG. 6;

FIG. 8 is a bottom view of the handle portion of FIG. 7;

FIG. 9 is a sectioned front elevational view of the handle portion of FIGS. 7 and 8;

FIG. 10 is a side elevational view of the handle portion of FIGS. 7-9;

FIG. 11 is a front elevational view of the handle portion of FIGS. 7-10;

FIGS. 12(a) and 12(b) illustrate views of the portable illuminator of FIGS. 2-5 and the handle portion of FIGS. 7-12 in an assembled and unassembled condition, respectively;

FIG. 17 is a partial sectioned side elevational view of the handle portion of FIGS. 7-16, including a portable illuminator disposed therein;

FIG. 18 is a partial bottom perspective section view of the handle portion and portable illuminator of FIG. 17;

DETAILED DESCRIPTION

Figure 1:
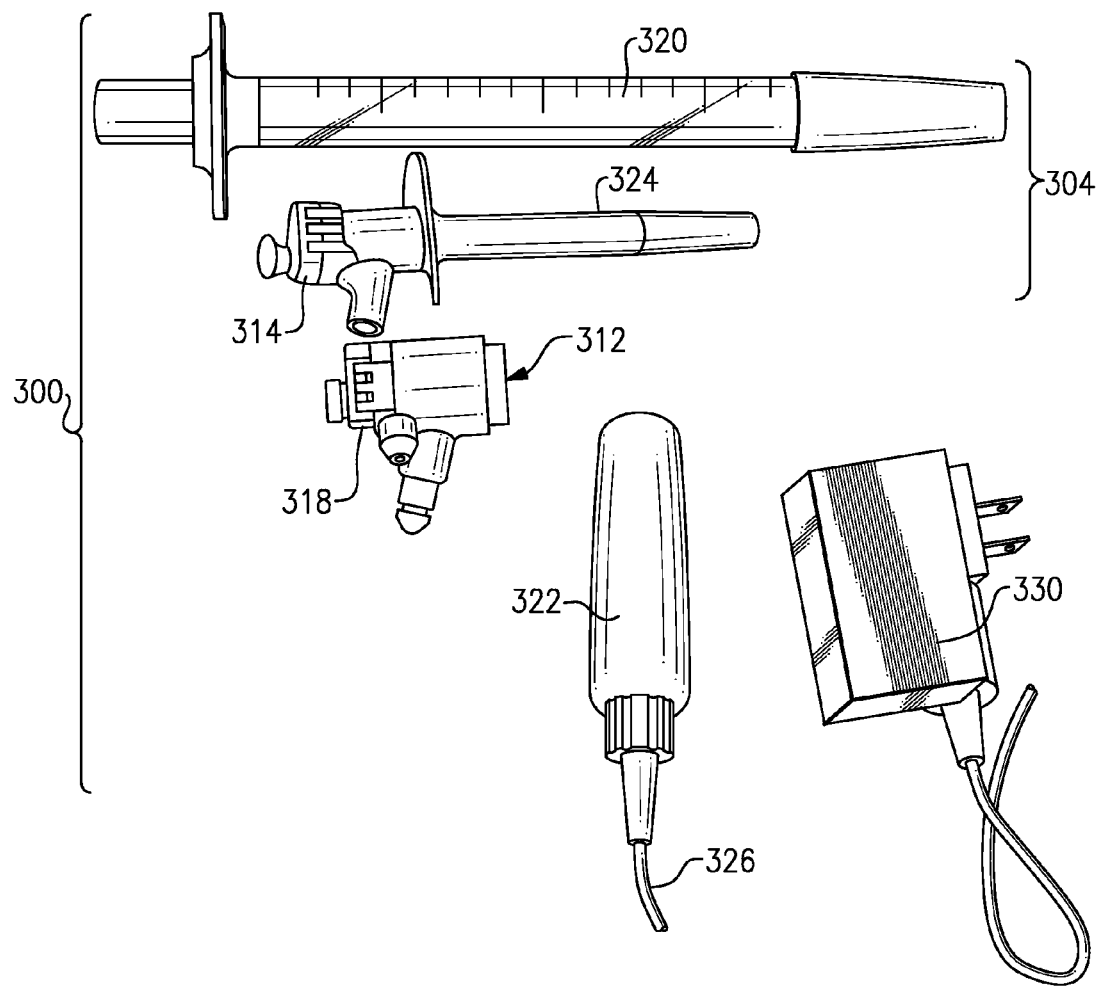
FIG. 1 is a perspective view of numerous prior art medical diagnostic instruments, including a tethered illumination assembly for use therewith.

The following discussion relates to various embodiments of a compact or portable illuminator that can be used in conjunction with either one or a plurality of various hand-held medical diagnostic instruments, including various designs of these instruments, in order to permit incorporation of the compact illuminator. Throughout the course of discussion, similar parts will be labeled with the same reference numerals for the sake of clarity of explanation. In addition, several terms such as "upper", "lower", "above", "within", "lateral", "upon", "below", "top", "bottom" and the like are used throughout this discussion in order to provide a suitable frame of reference with regard to the accompanying drawings. It should be understood that these terms are not intended to be limiting, however, except where so specifically indicated.

Referring to FIG. 1 and for background purposes, there is first shown a group 300 of prior art hand-held medical diagnostic instruments, in this instance, a sigmoidoscope 304 and an anoscope 312. Each of the depicted diagnostic instruments 304, 312 in this group 300 is commonly defined by an instrument head 314, 318. Each instrument head 314, 318 includes at least one engagement feature enabling the releasable attachment of a handle portion 322 to a lower end thereof and a sigmoidoscope body (such as 320, 324 that are selectively attachable to the distal end of the sigmoidoscope instrument head 314). The handle portion 322 includes a cord 326 and transformer 320 that permits a tethered connection to a non-compact power source (such as an AC wall power supply, not shown), to energize a light source (not shown) provided in the handle portion 322 in order to permit light to be effectively transmitted to the instrument head 314, 318, thereby permitting patient examination. Details of a tethered illuminator assembly of this type are described for example, in U.S. Patent Application No. 2004/0186355 to Strong et al.

In general, the following embodiments relate to various hand-held diagnostic instruments having a handle portion defined by an open lower or bottom end and a hollow interior including an elongated cavity, which is sized and configured to releasably retain a compact illuminator. As discussed in greater detail below, the handle portion can be releasably attached to the remainder of a medical diagnostic instrument or made integral therewith. Alternatively, the handle portion can also be one of disposable (single use or single-patient use) and reusable. Prior to discussing the representative handle portion designs and their salient features, a description of an exemplary portable illuminator for use therewith follows.

Referring to FIGS. 2-5, the exemplary portable illuminator 20 is defined by a housing 24 having a substantially hollow interior that is sized to retain a number of components, as described below, including at least one portable light source and at least one portable power supply.

As described herein, the portable light source is a miniature white LED 28, such as, for example, those manufactured and sold by Nichia America, Inc. and Lumileds, Inc., while the portable power source includes at least one rechargeable battery 32, such as, for example, a Model UF612248PJFH lithium-ion battery manufactured by Sanyo Corp, the battery having suitable characteristics to sufficiently power the LED 28. The use of an LED 28 is preferred to make the illuminator "portable"; that is, such that it is not tethered (i.e., corded) and therefore does not require a non-portable power source, such as a wall transformer or AC power supply, and wherein the illuminator 20 functions as an integrated unit. To that end, however, it should be readily apparent that other forms of portable power sources, such as other forms of batteries or alternative sources of energy; for example, capacitors that are capable of being recharged for portable use, can be substituted.

The housing (also commonly referred to throughout as a "body section") 24 of the portable illuminator 20 according to this embodiment is manufactured from a lightweight, durable material, such as a moldable plastic, and is further defined by an upper housing portion 36 and a lower base portion 40. The housing 24 is made from a two piece shell-like structure that is ultrasonically welded or otherwise connected together. Other structural forms and shaping of the housing 24, however, should be readily apparent. For example and alternatively, a battery compartment could be provided having a removable cover (not shown), if desired, for removing and replacing the rechargeable battery 32, as needed.

The upper housing portion 36 is defined by a relatively flat, thin (low profile) enclosure having a substantially constant thickness and width wherein each of these dimensions is approximately equal to that of the contained battery 32. According to this embodiment, the lower base portion 40 is significantly wider than that of the upper housing portion 36, the former expanding from a maximum width adjacent a bottom surface 165 to a minimum width adjacent the bottom of the upper housing portion. The transition from the top to the bottom of the lower base portion 40 according to this exemplary embodiment takes the form of a substantially trapezoidal shape, as viewed from the side of the illuminator 20; see FIG. 4. This specific transition provides an ergonomic design and further assists in positioning and retaining the illuminator 20 within the receiving cavity defined in the handle section of at least one medical diagnostic instrument, as described in greater detail below, as well as a charging station (not shown) used to recharge the rechargeable battery 32. This transition also assists in the removal of the illuminator 20 from the handle portion, as described in greater detail below.

The LED 28 is retained herein within a substantially cylindrical region 44 projecting from the top of the upper housing portion 36. The cylindrical projecting region 44 preferably surrounds the lens envelope (not shown) of the LED 28, as well as a front lens element 34, wherein the cylindrical projecting region protects both the LED and lens element from shock, impact and associated loads.

The LED 28 is further housed within a retaining structure 49 wherein the electrical contacts of the LED are attached to a flexible circuit assembly 96, one end portion of which covers a heat sink 54. The heat sink is being made from aluminum or other material with suitable heat conductivity properties that is disposed between the battery 32 and LED 28, wherein each of the foregoing elements are disposed within the upper housing portion 36. The remainder of the flexible circuit assembly 96 extends downwardly across one facing side of the illuminator 20 to the bottom of the lower base portion 40. The electrical contacts (not shown) extending from the LED 28 are attached to the flexible circuit assembly 96 using a thermal epoxy, such as, for example, Emerson Cuming Stycast 2850, such that the contacts also conduct heat away from the LED 28 to the heat sink 54.

The retaining structure 49 can include an interior reflective surface (not shown) used to assist in directing light towards the front lens element 34. According to this embodiment, the heat sink 54 includes a lateral recess 56 that permits the inclusion of a retention pin 58 having a beveled end 62 that extends outwardly from one lateral side of the housing 24. The beveled end 62 of the retention pin 58 is biased outwardly by means of a spring 60. According to this embodiment a spacer 94, having a layer of soft foam material provided on upper and lower facing sides thereof, is disposed between the bottom of the heat sink 54 and the battery 32, this spacer also providing isolation between the heat sink 54 and battery 32 from impact and shock loads being applied to the illuminator 20.

Figure 2:
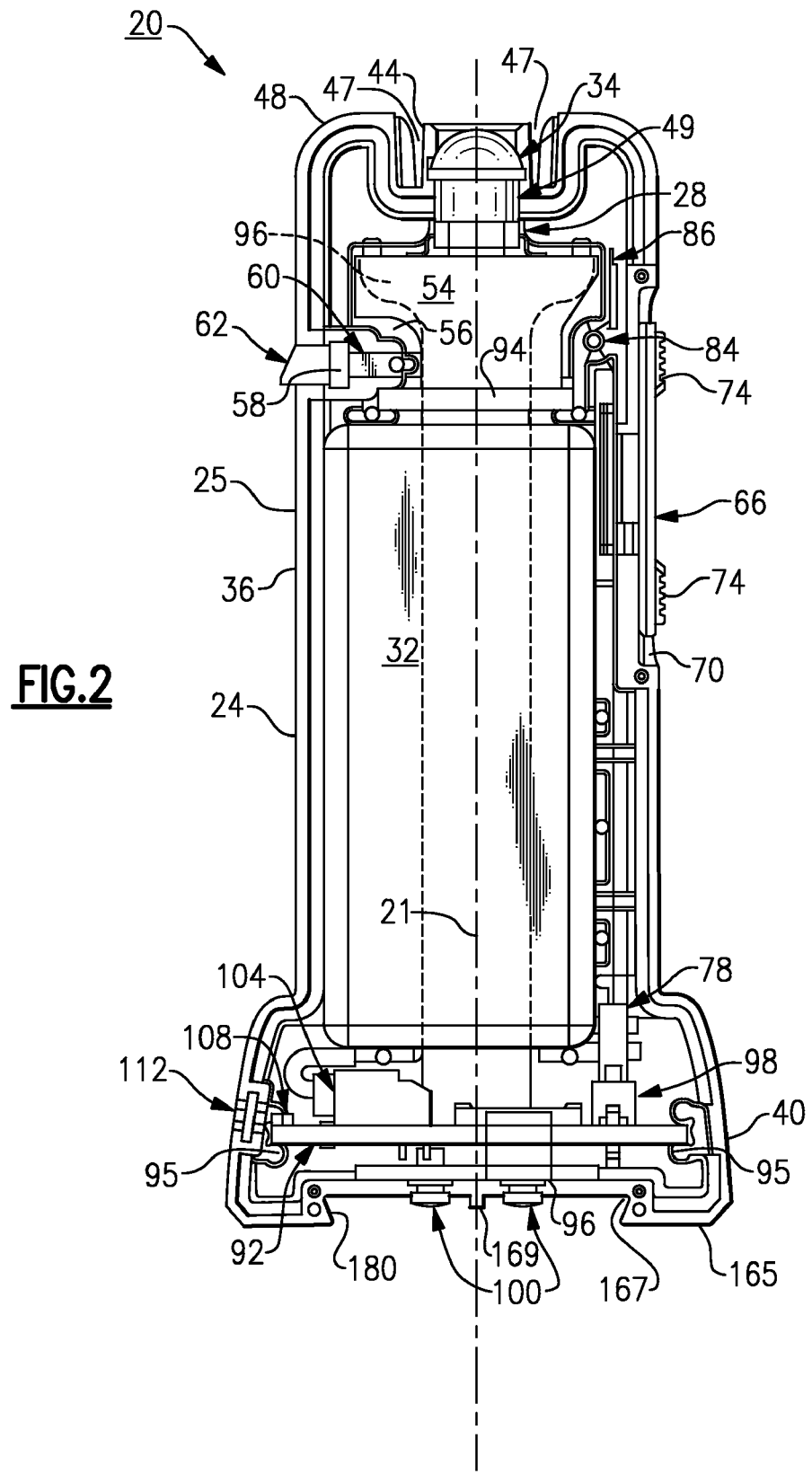
FIG. 2 is a side view, shown in section, of a portable illuminator for use with at least one medical diagnostic instrument.
Figure 3:
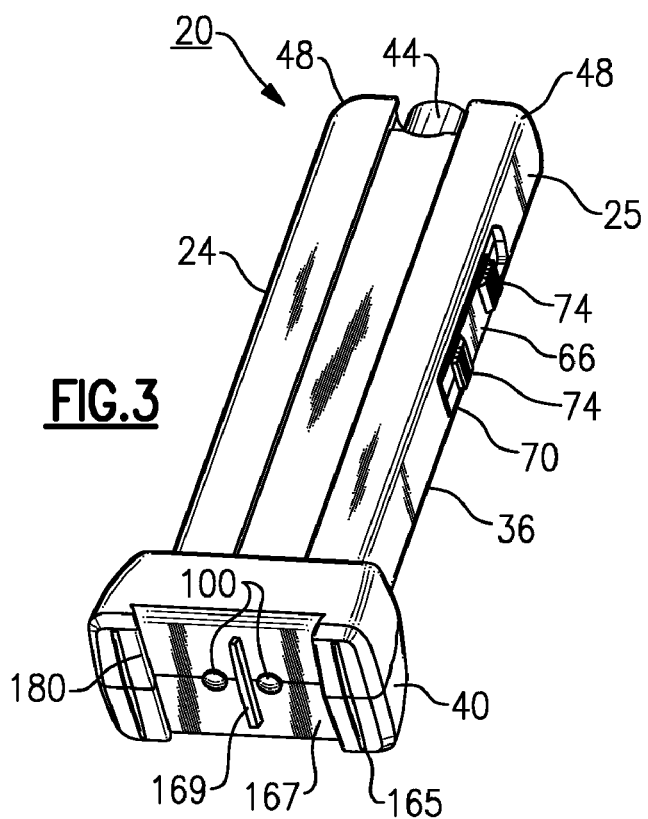
FIG. 3 is a bottom perspective view of the portable illuminator of FIG. 2.
Figure 4:
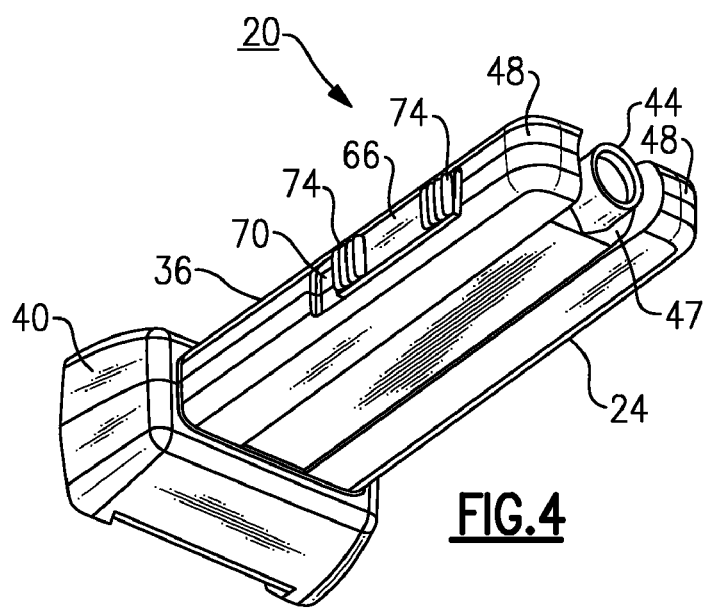
FIG. 4 is a front perspective view of the portable illuminator of FIGS. 2-3.

As noted above, a flexible circuit assembly 96 is provided in relation to the LED 28, an upper end portion of this assembly being folded about the heat sink 54 and extending along the interior wide side of the illuminator 20. On the lateral side 25, FIG. 2, opposite that of the beveled retention pin 58, a slide switch 66, FIG. 2, is vertically arranged within a slotted area 70 such that the switch is mainly recessed and does not extend beyond the exterior of the lateral side 25 with the exception of a pair of tabs 74 disposed at respective ends of the exterior surface of the switch.

The slide switch 66 is biased in an off position by means of a switch spring 78 attached to a leaf spring 86 extending along substantially the entire lateral side of the housing 24. The leaf spring 86 is formed into a bump onto which a dowel pin 84 is disposed. The lower end of the leaf spring 86 is attached to the switch spring 78, the switch spring being further disposed in relation to a switch 98 that is attached to a printed circuit board 92. Downward movement of the slide switch 66 from the off position, such as by means of finger pressure against one of the tabs 74, causes corresponding movement of the leaf spring 86 sufficient to cause the switch spring 78 to be loaded in compression to engage the switch 98, which provides tactile feedback to the user and engaging same, thereby completing the electrical connection between the LED 28 and the battery 32 and energizing the LED. Additional movement of the slide switch 66 overcomes the detent provided by the dowel pin 84 to hold the switch in an energized position. Heat that is generated by the LED 28 and the flexible circuit assembly 96 is dissipated by the heat sink 54.

In addition, the lower base portion 40 further permits the printed circuit board 92 to be supported horizontally (i.e., perpendicular to the major dimension of the battery 32) and retained by a pair of channels 95. The lower end portion of the flexible circuit assembly 96 is disposed in overlaying relation over the bottom of the printed circuit board 92, this portion of the flexible circuit assembly including a pair of integral electrical contacts 100 that extend outwardly from the bottom of the housing 24. Providing each of the electrical contacts 100 integrally on the flexible circuit board assembly 96 provides savings in terms of the overall space envelope of the portable illuminator 20.

With regard to the components included on the printed circuit board 92, the electrical contacts 100 employ a bi-polar diode bridge, thereby enabling the illuminator 20 to be oriented relative to a suitable interface with regard to at least one electrical device, as described in greater detail in U.S. Ser. No. 11/731,631, the entire contents of which are herein incorporated by reference. Additionally, the circuit board 92 includes a power conversion means, for example, a buck-boost constant current LED driver, such as Model LTC 3453UF; which drives the LED 28 with substantially constant current over the useful voltage limits of the contained battery 32 (e.g., 4.2 volts for a charged battery, 2.4 volts for a nearly depleted battery). Other suitable means, however, can alternatively be provided. A battery connector 104 is also connected to the top surface of the printed circuit board 92 and the battery 32, wherein the circuit board further includes a protection or safety circuit to prevent shorting and over charging of the contained battery, such as, for example, a Model UCC 3952-PW-1, manufactured by Texas Instruments, Inc. In addition to the above, a current charge limiter is also included to prevent the portable illuminator 20 from being charged by an electrical device (not shown) that is connected to the electrical contacts 100 while the illuminator 20 is enabled. A low-battery LED indicator assembly 108, attached to the printed circuit board 92, includes a window 112 that is disposed in a lateral side of the lower base portion 40. The window 112 provides an indication to a user when the contained battery 32 is either charged or in need of charge, such as, for example, through flashing or a change in color of the LED, in a manner that is known to those in the field. For example, the low-battery LED indicator assembly 108 can illuminate one color (e.g., yellow) through the window 112 when 10 minutes of "on" time remains and a second color (e.g., red) when 5 or less minutes of time remains. It should be readily apparent that other similar configurations can be contemplated.

Referring back to the structure of the illuminator housing 24, the upper housing portion 36 includes a pair of shoulders 48 spaced evenly apart from the cylindrical projecting region 44 on opposing lateral sides thereof. Each of the shoulders 48 extends upwardly, according to the embodiments described herein, such that the top surface of each shoulder is substantially coplanar with or slightly above the top of the cylindrical projecting region 44. The shoulders 48 therefore provide an additional means to protect the portable illuminator 20, and particularly the contained LED 28 and lens element 34, from impact, shock and associated loads. By including the shoulders 48 and the foam spacer 94, and based on the compact design of the herein described illuminator, the herein described illuminator 20 can withstand damage from drops from as high as 4 feet. The shoulders 48 and the substantially cylindrical projecting region 44 also permit the portable illuminator 20 to be inserted only to a predetermined distance within a handle portion of a diagnostic instrument as described in greater detail below.

Figure 5:
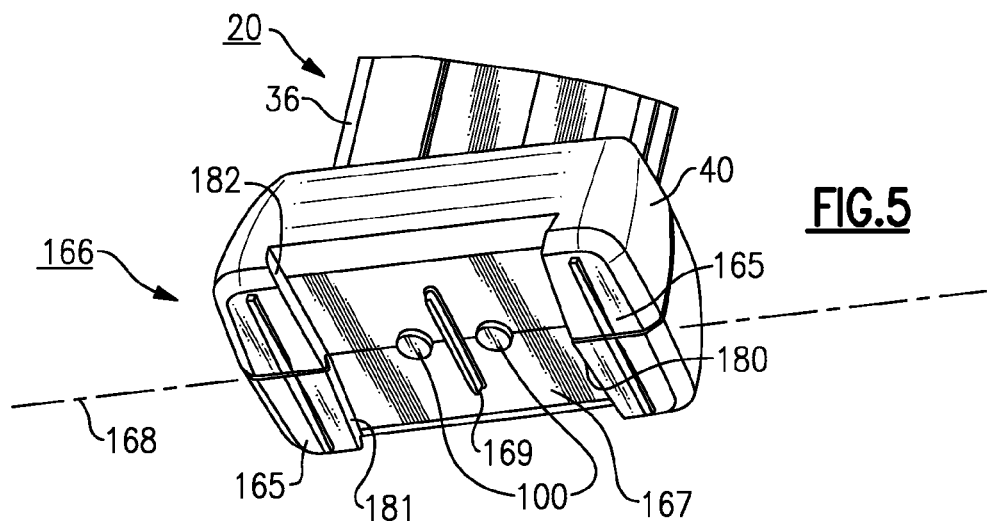
FIG. 5 is an enlarged bottom perspective view of the portable illuminator of FIGS. 2-4.

According to this specific embodiment, the bottom surface 165 of the portable illuminator 20 includes a recessed surface portion 167, defining an interface 166 that includes the pair of electrical contacts 100 extending outwardly therefrom. A transverse rib 169 is further provided between the pair of electrical contacts 100 and disposed in approximately the center of the bottom surface 165. A pair of side walls 180 defines the transition between the recessed surface portion 167 and the bottom or base surface 165 of the illuminator 20. Each of the side walls 180 is inwardly angled, according to this embodiment; that is, each of the side walls further comprise a pair of angled segments 181, 182, extending laterally outward relative to a centerline 168 that runs perpendicular to the axis of the transverse rib 169. This interface 166, FIG. 5, is matingly engageable with various electrical devices, as described in greater detail in previously incorporated U.S. Ser. No. 11/731,631, including an auxiliary power module plug (not shown) and a charging station (not shown), wherein the interface enables the recessed electrical contacts 100 to remain substantially clean during use. It should also be noted that the herein described illuminator 20 can also be used independently without connection to a medical diagnostic instrument for purposes of use as a portable examination light.

Figure 6:
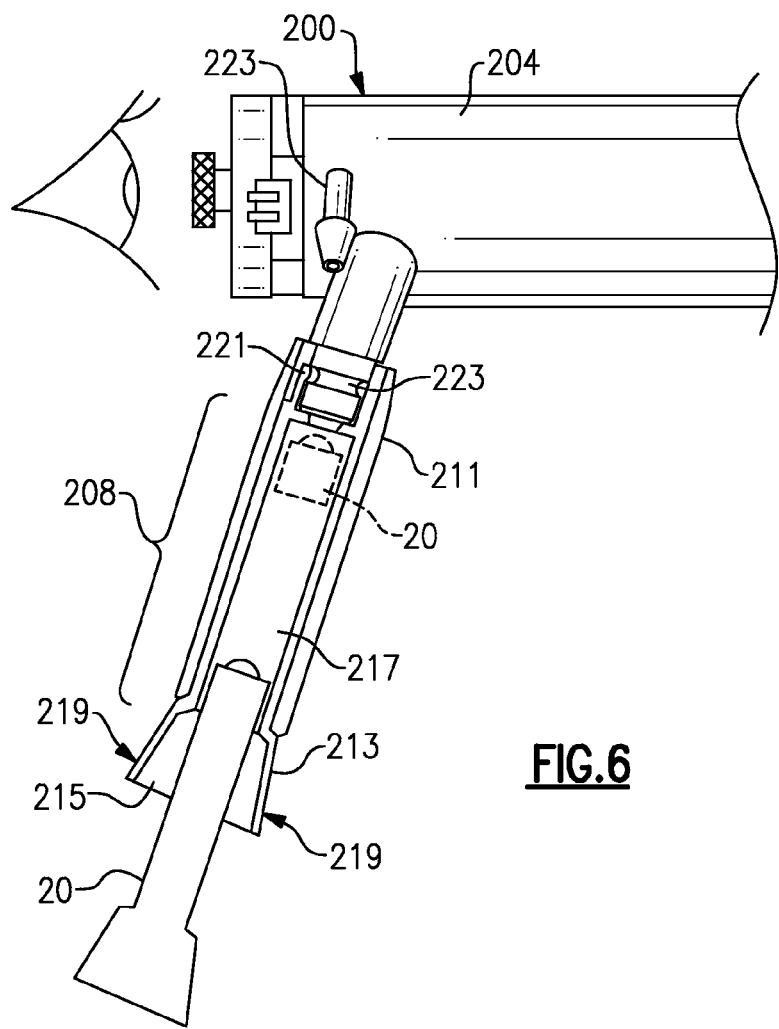
FIG. 6 is a schematic partial view of a medical diagnostic instrument assembly in accordance with one embodiment, including a medical diagnostic instrument having a handle portion that is configured to substantially receive the portable illuminator of FIGS. 2-5 (shown as partially inserted into the handle portion)
Figure 6A:
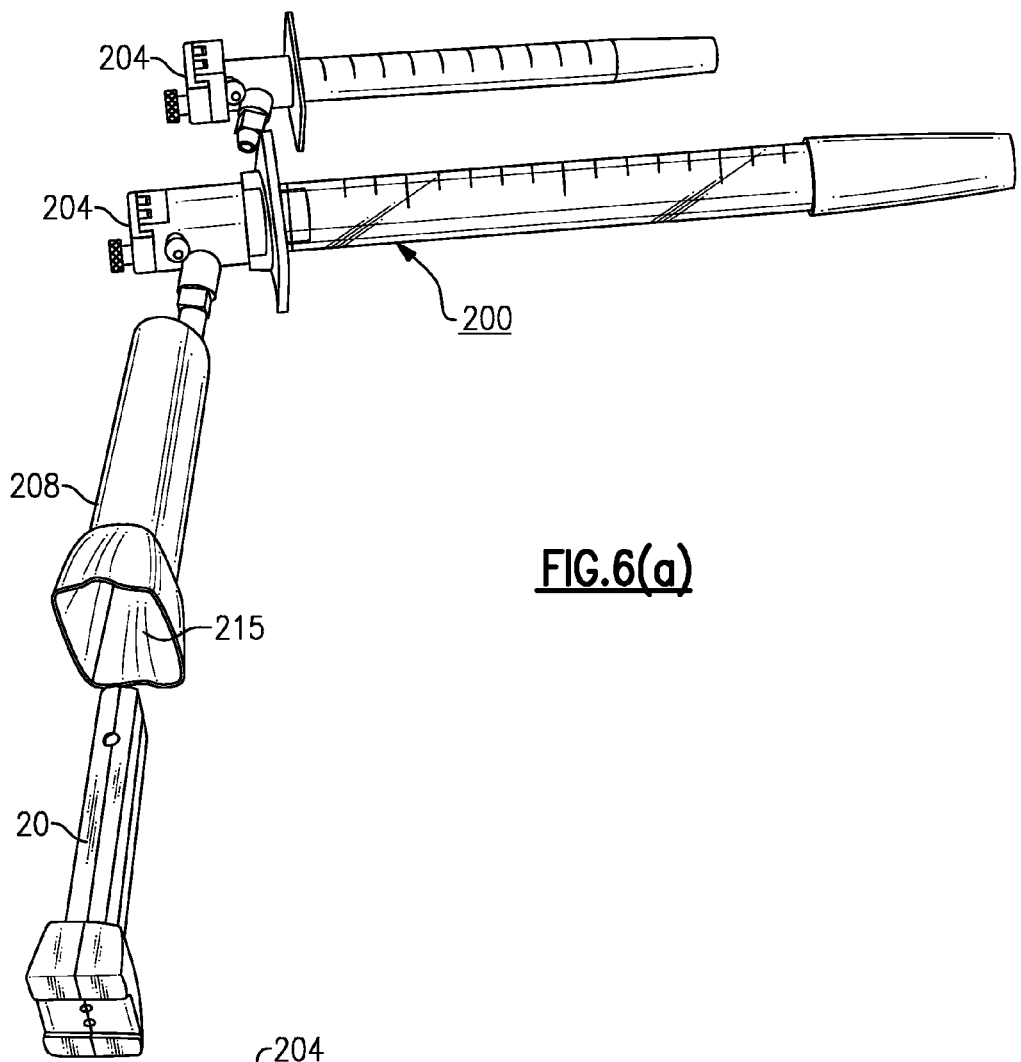
FIG. 6(a) illustrates the medical diagnostic instrument assembly shown schematically in FIG. 6, as unassembled.
Figure 6B:
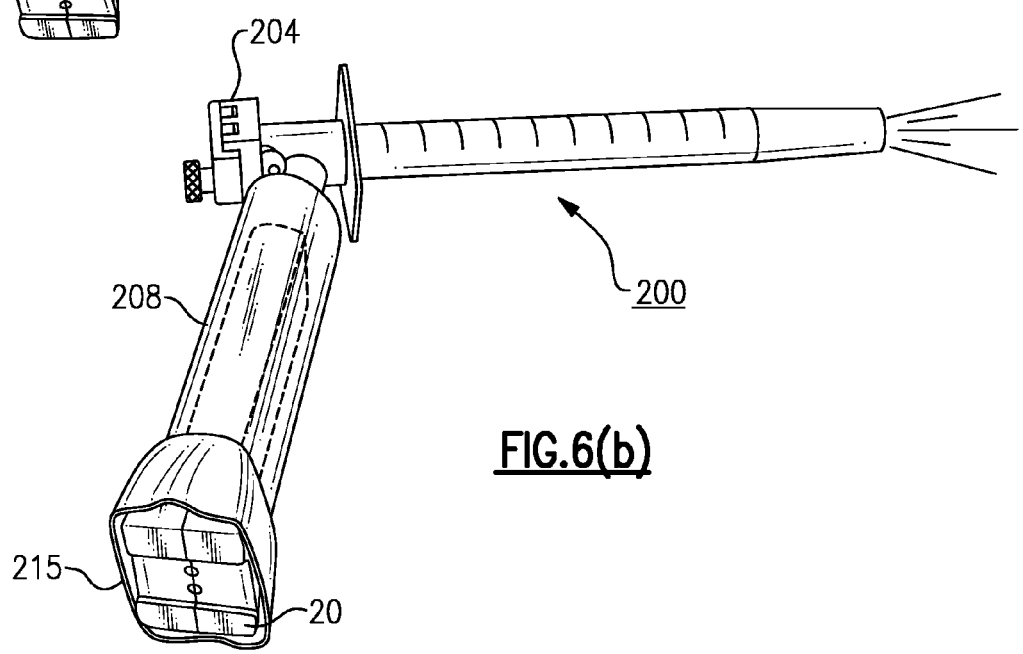
FIG. 6(b) illustrates an assembled version of the instrument assembly of FIG. 6(a)
Figure 28:
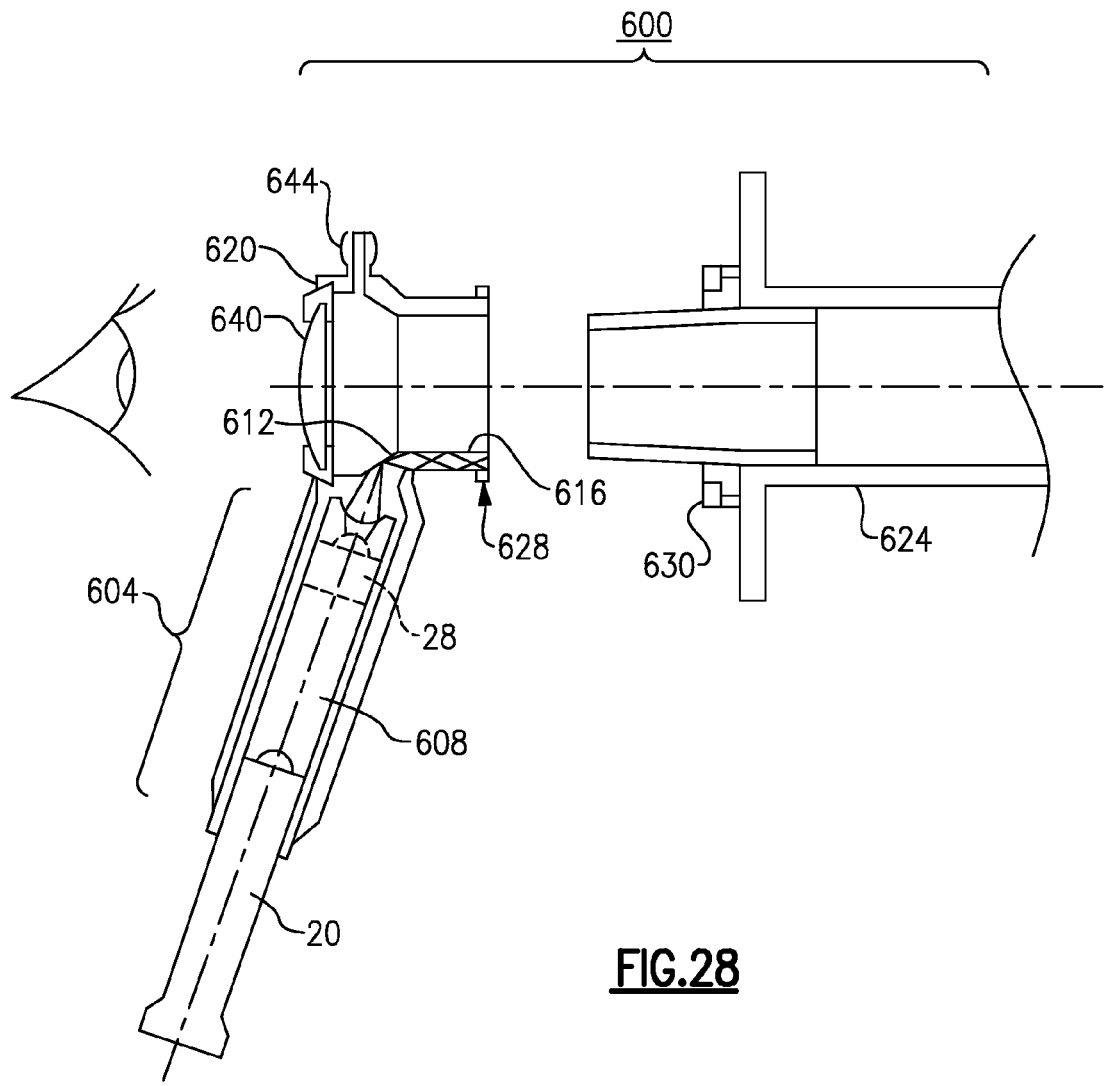
FIG. 28 is a schematic view of a medical diagnostic instrument assembly in accordance with an alternative embodiment, the assembly including a medical instrument having a handle portion that is configured to receive the portable illuminator (shown partially inserted into the handle portion) of FIGS. 2-5.

Having described the portable illuminator 20 and referring to FIGS. 6, 6(a) and 6(b), there is shown an exemplary embodiment of a hand-held medical diagnostic instrument configured to employ same. According to this embodiment, the medical diagnostic instrument, in this case, a sigmoidoscope 200, includes an elongated instrument head 204 and a coupled handle portion 208. The handle portion 208 according to this embodiment is releasably attached or coupled with an engagement portion 223, such as a post projecting outwardly from the bottom of the elongated instrument head 204. In passing, it should be noted the releasability of the handle portion to the remainder of the instrument is a desirable though is not an essential feature for purposes of retaining the illuminator 20. That is, the handle portion could also be made integral with one or the remainder of any of a plurality of medical diagnostic instrument(s), as shown in FIG. 28.

An exemplary handle portion 208 is depicted in FIGS. 7-11, which is used in conjunction with the portable illuminator 20, as further shown in an assembled condition in FIGS. 12 and 14-18. According to this specific embodiment, the handle portion 208 is made from a formable, durable, lightweight plastic, such as polyethylene or other suitable material, and can be manufactured, such as through an injection-molding or blow-molding process. In one variation, the handle portion 208 can be treated with a so-called "green" (i.e., biodegradable) material; for example an additive such as Nature Works 3001 PLA, although other materials could also be contemplated provided they are lightweight, preferably biocompatible and relatively durable. In this instance, the additive enables the treated handle portion 208 to become a biodegradable end product over time.

Figure 12:
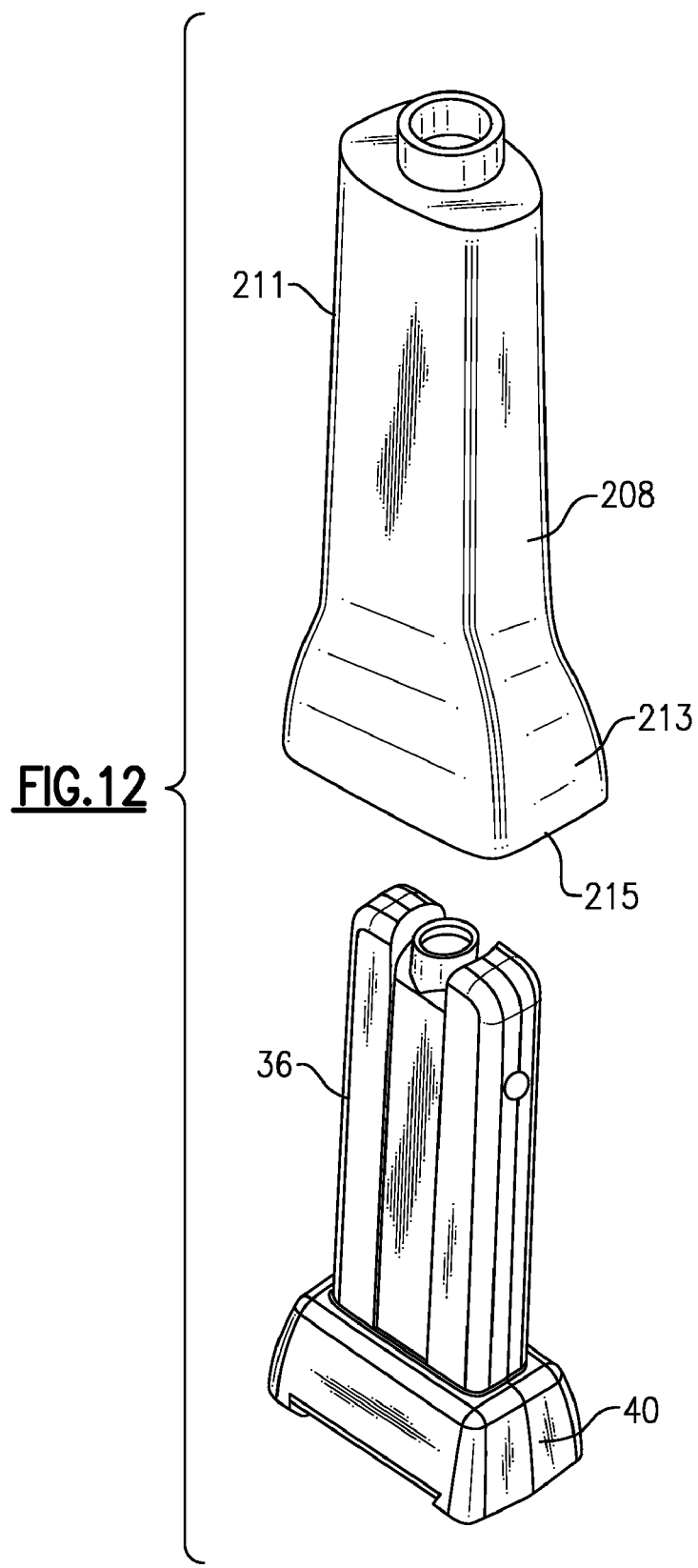
FIG. 12 is a partially exploded view illustrating the portable illuminator of FIGS. 2-5 and the handle portion of FIGS. 7-11.
Figure 14:
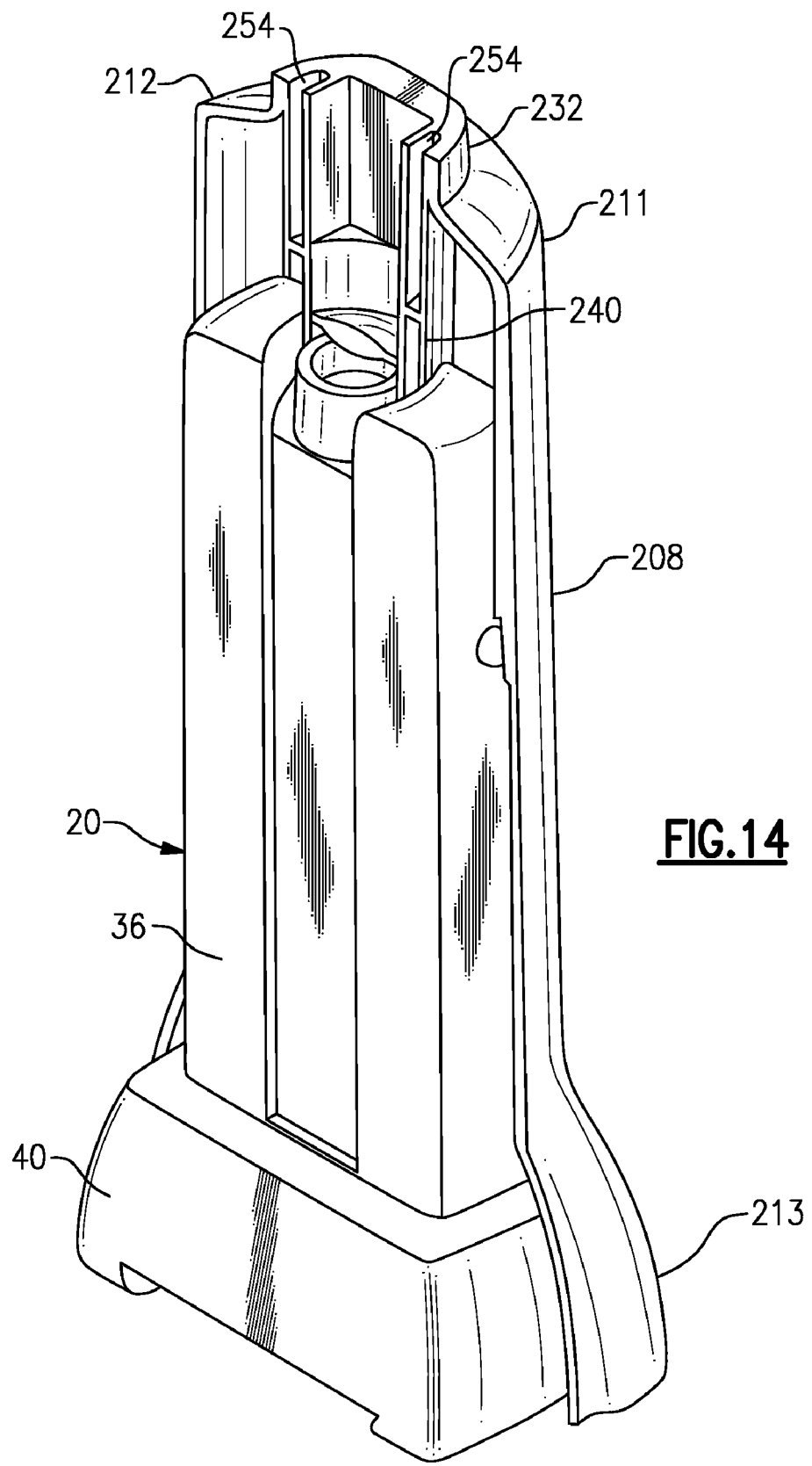
FIG. 14 is a partial front perspective view of the compact illuminator as positioned in the handle portion of FIGS. 7-13, the handle being shown partially cutaway.
Figure 15:
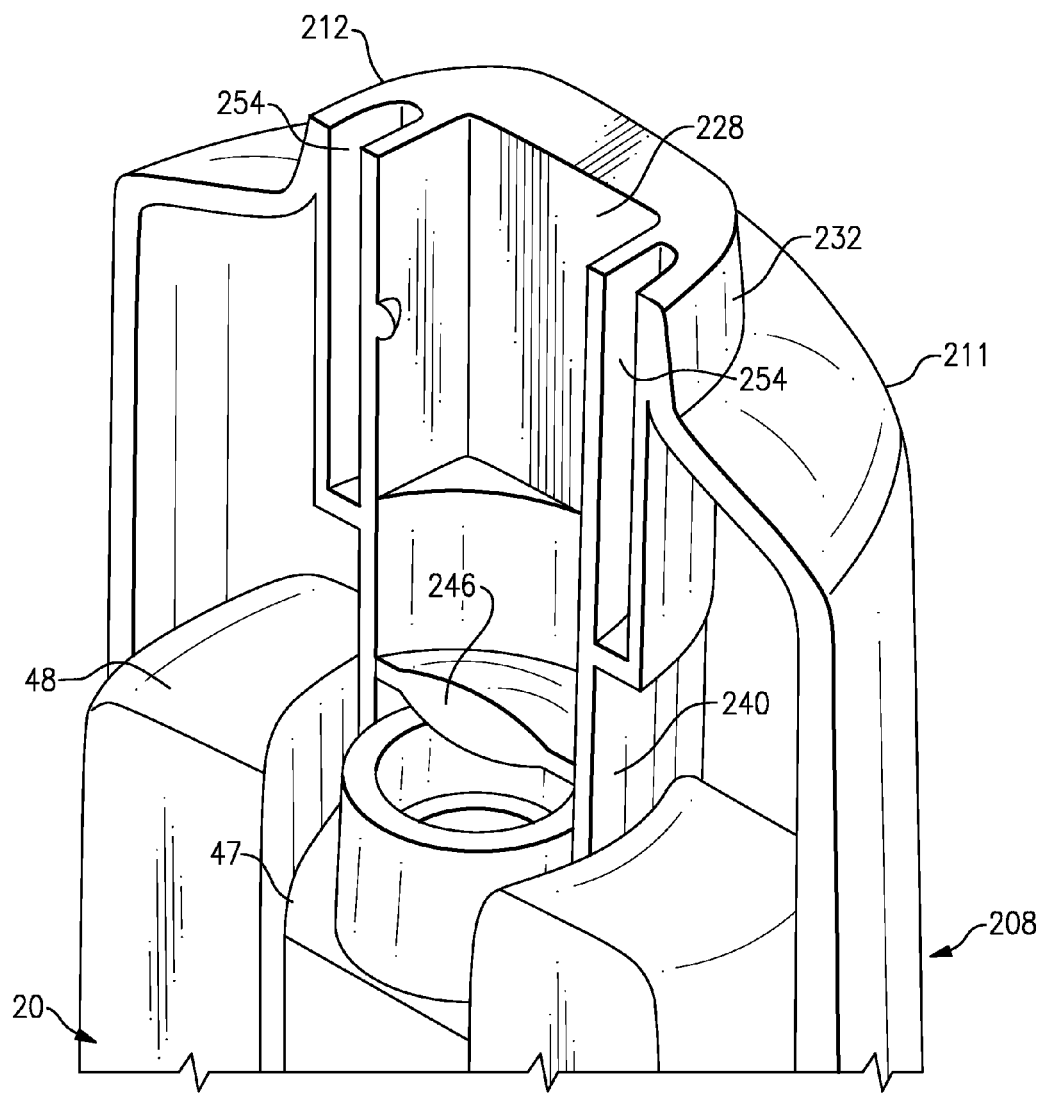
FIG. 15 is an enlarged section view of the cutaway handle portion of FIG. 14, including an enclosed portable illuminator.
Figure 16:
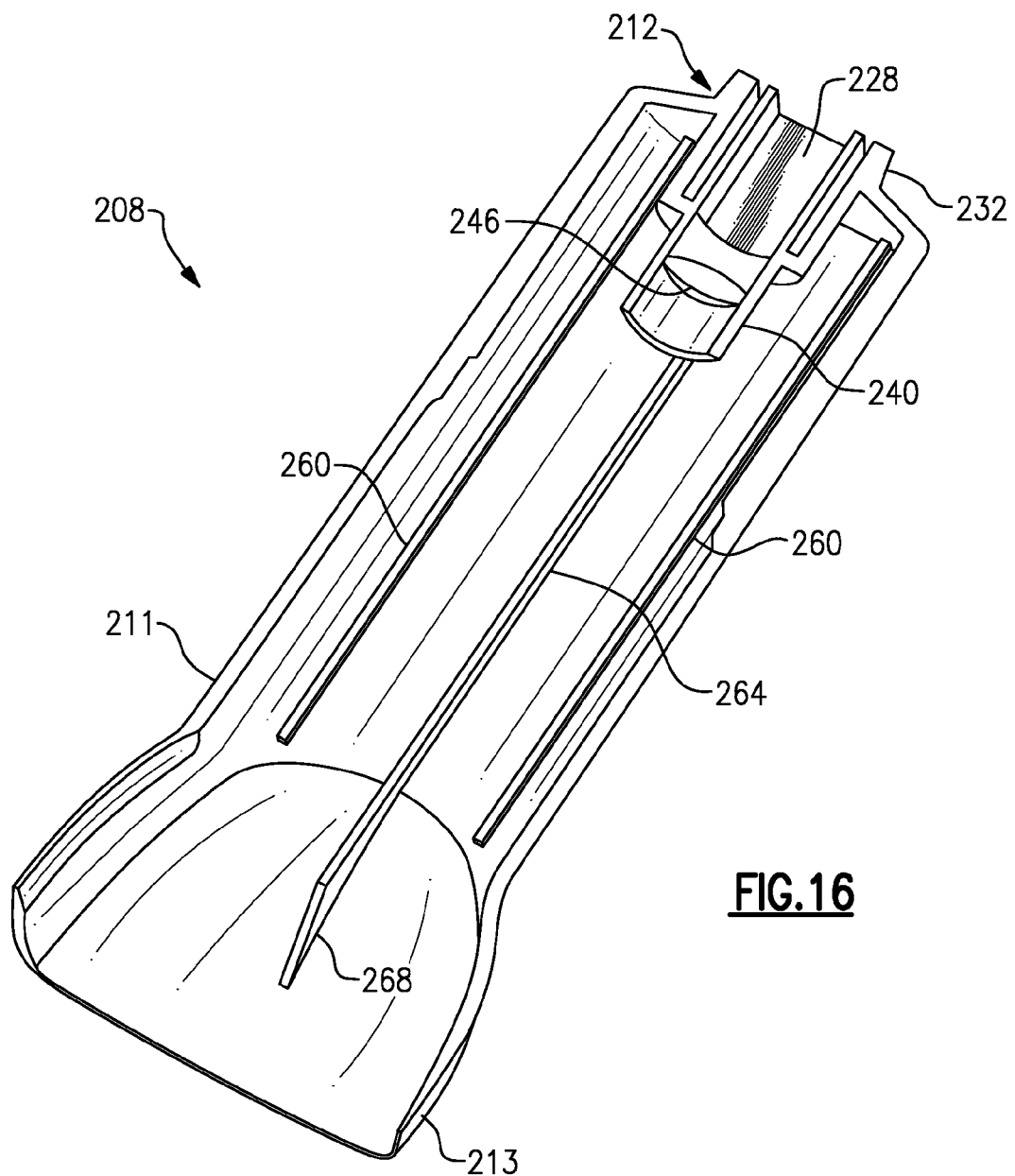
FIG. 16 illustrates a cutaway partial perspective view of the handle portion of FIGS. 7-15.

The handle portion 208 according to this embodiment and shown more particularly in FIGS. 7-11 is generally defined by an upper coupling housing section 211 and a lower receiving section 213, the latter including an open end 215 extending into an elongated receiving cavity 217, FIGS. 9 and 12(a). The upper coupling and lower receiving housing sections 211, 213 of the handle portion 208 according to this embodiment substantially mimic the shape (i.e., the upper housing portion 36, FIG. 2, and lower base portion 40, FIG. 2) of a portable illuminator 20, FIG. 6, which can be releasably introduced into the elongated receiving cavity 217, FIG. 12(a). As shown in FIGS. 6, 12 and 14, the receiving cavity 217 is sized to substantially accommodate the entire length of the portable illuminator 20.

The upper coupling section 211 is further defined by a mating upper end 212, more clearly shown in FIGS. 7 and 10-15, which projects outwardly from the top of the handle portion 208. An interior cylindrical section 232 of the mating end 212 comprises a center cavity 228 which is formed therein, the section further comprising an upper portion 250 and a tubular lower portion 240 that includes a lower surface 246. The center cavity 228 extends through the entirety of the upper portion 250 and the tubular lower portion 240 with the exception of the lower surface 246, which according to this exemplary embodiment is itself a thinned section or web of the molded handle portion 208. The lower surface 246 provides two functions. First, this surface in combination with the remainder of the top of the handle portion provides a fluid seal with respect to the interior of the instrument head when the handle portion is attached thereto. Second, the thinned material of the lower surface provides optical transmissivity and enables optical coupling between the contained light source of the portable illuminator 20 and the instrument head 204. The remainder of the herein described handle portion 208, however, is generally opaque while the thinning of the plastic web forming the lower surface 246 produces a generally transparent structure. Additionally, this thinned surface can also be shaped in order to provide optical power; in this case, the surface is shaped as a lens.

Figure 13:
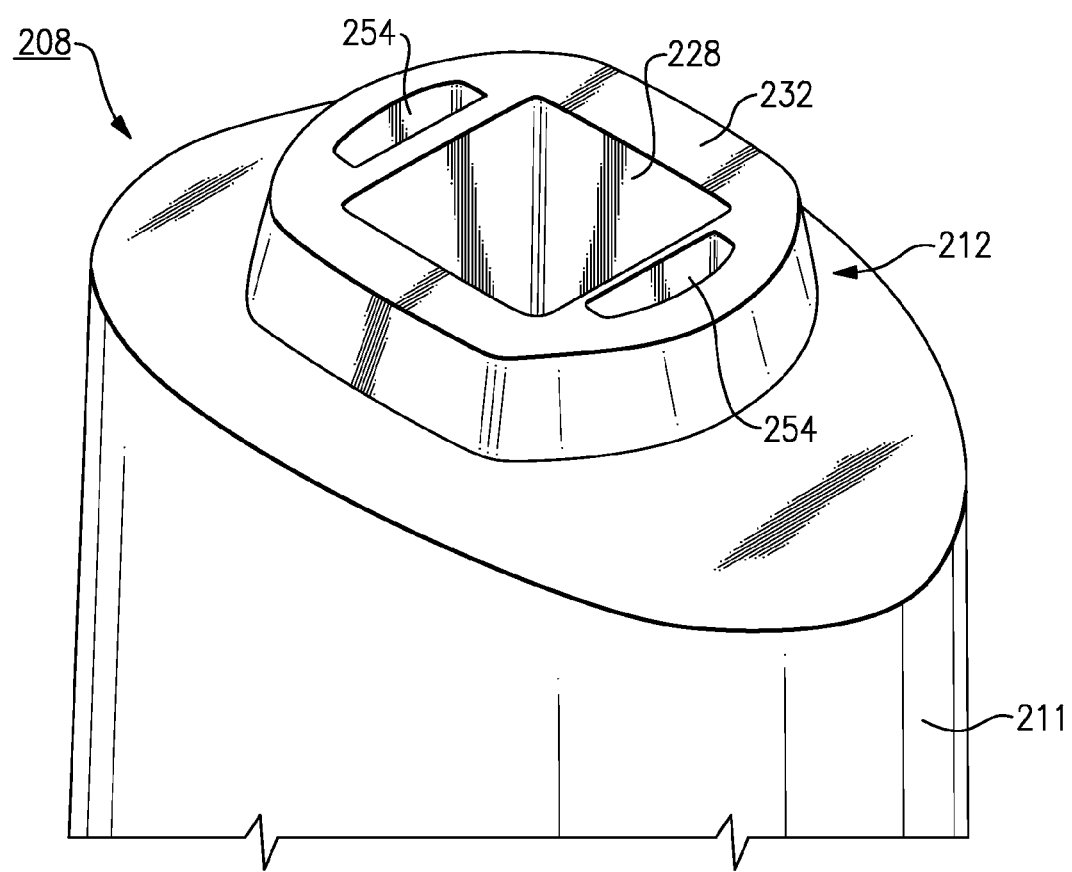
FIG. 13 is an enlarged view of the upper mating end of the handle portion of FIGS. 7-12.

The upper coupling section portion 250 of the herein described upper coupling section 211 further includes a pair of slots 254, FIG. 13, that are formed on opposite sides of the center cavity 228. Each of the slots 254 creates flexures 221 in conjunction with the center cavity 228 that are used for engagement with an engagement feature 223, FIG. 6, of the diagnostic instrument 200, as described below.

As shown in FIG. 9, the lateral interior sides of the handle portion 208 within the receiving cavity 217 includes a set (e.g., four, but only two actually shown in this cutaway view) of parallel spaced guide rails 260 that extend substantially along the entire length of the upper housing section 211, as well as a pair of center rails 264 (only one shown in this cutaway figure) along opposite lateral sides that additionally extend partially into the lower receiving section 213. The center rails 264 are each defined by a lower ramped surface 268, the purpose of which will be described in greater detail below. Additionally, the foregoing rails 264 also provide a dual function in that these surfaces act as fins so as to provide a means for heat dissipation as to a contained compact illuminator 20, FIG. 2.

In terms of assembly and as shown in FIGS. 6, 12(a), 12(b), 14 and 15, the portable illuminator 20 is sized to fit substantially within the elongated receiving cavity 217 of the handle portion 208 wherein the cylindrical projecting region 44 at the top of the upper housing portion 36 is sized to fit within the confines of the lower tubular section 240 of the mating end 212. The spacings 47, FIG. 2, between the shoulders 48 of the illuminator 20 form stops with the tubular lower section 240 and bring the cylindrical projecting region 44 and the contained LED 28, FIG. 6, into optical alignment with the lower surface (lens) 246. The parallel rails 260 assist in guiding the illuminator 20 into position, wherein the illuminator can be introduced in one of two different (e.g., opposite) axial orientations that are 180 degrees apart from one another, enabling versatility in assembly by an operator (not shown). According to this embodiment, an interior tooth or prong (not shown) that is provided on an interior surface of the elongated cavity 217 provides positive engagement when the illuminator 20 has been fully engaged within the handle portion against the retention pin 58, FIG. 2.

The post-like engagement feature 223, FIG. 6, of the instrument 200 extends outwardly from the bottom of the instrument head 204 and is attached to the mating end 212 such that the engagement feature is fitted within the center cavity 228 of the upper portion 250 thereof. As the post-like engagement feature is fitted, the flexures 221 defined by the slots 254 outwardly flex and permit the engagement feature to be positively engaged in a releasable fashion.

In addition and according to one version, sliding the portable illuminator 20 axially into position in the elongated receiving cavity 217 of the handle portion 208 causes the contained LED 28, FIG. 2, to be energized automatically as a result of the movement of the biased slide switch 66, FIG. 2, and as further described in U.S. Ser. No. 11/731,631, and U.S. Ser. No. 11/731,189, incorporated by reference herein in their entirety. This is further shown in FIG. 6(b), upon movement a predetermined distance within the receiving cavity 217.

The portable illuminator 20 can be selectively released from the herein described assembly by squeezing the lower portion 213 of the handle portion 208, as shown by arrows 219, FIG. 6. The flexible nature of the handle portion 208 produces localized inward deformation of the lower portion 213 relative to the remainder of the handle portion 208, causing the lower base portion 40, FIG. 2, of the portable illuminator 20 to be guided from the confines of the receiving cavity 217 through the open end by engagement by the ramped surfaces 268 of the rails 264 against the illuminator housing overcoming the force of the interior tooth (not shown). As the portable illuminator 20 is caused to move outwardly from the handle portion 208 of the instrument 200, the biased slide switch 66 is automatically moved to a neutral position that deenergizes the contained LED 28.

Advantageously, the herein described handle portion 208 effectively becomes a protective sheath for the contained portable illuminator 20 during examination and protects the illuminator from fluid or other cross contamination from the patient. Following use and according to this version, the handle portion 208 can be releasably removed from the remainder of the diagnostic instrument 200 by releasing engagement feature 223 from the mating end 212 wherein the handle portion can then be discarded. In one version, the engagement slot 254 and flexures 221 of the mating end 212 of the handle portion 208 can be made such that disengagement from the instrument 200 disables these features, rendering the handle portion 208 ineffective and thereby preventing reuse after a single attachment/engagement or after a few or predetermined number of attachments to the instrument 200.

Figure 19:
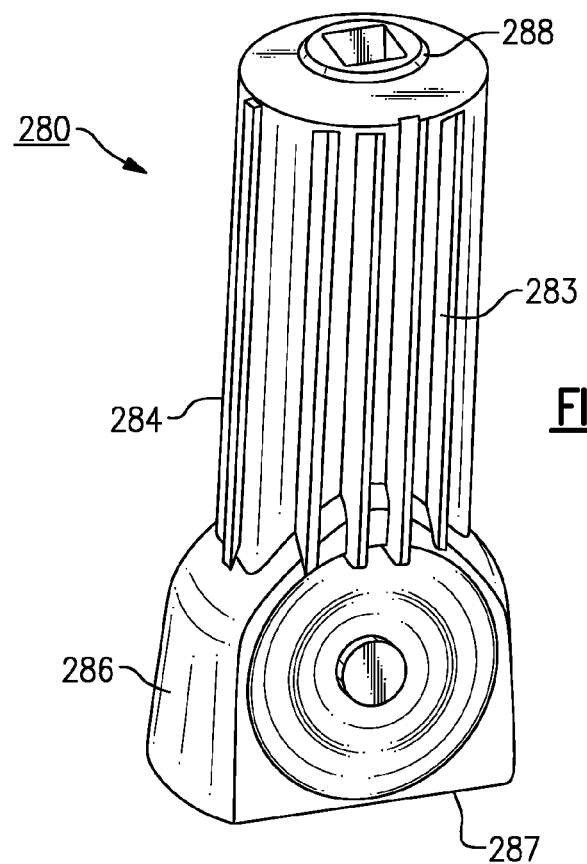
FIG. 19 is a front perspective view of a handle portion which is made in accordance with another embodiment.
Figure 20:
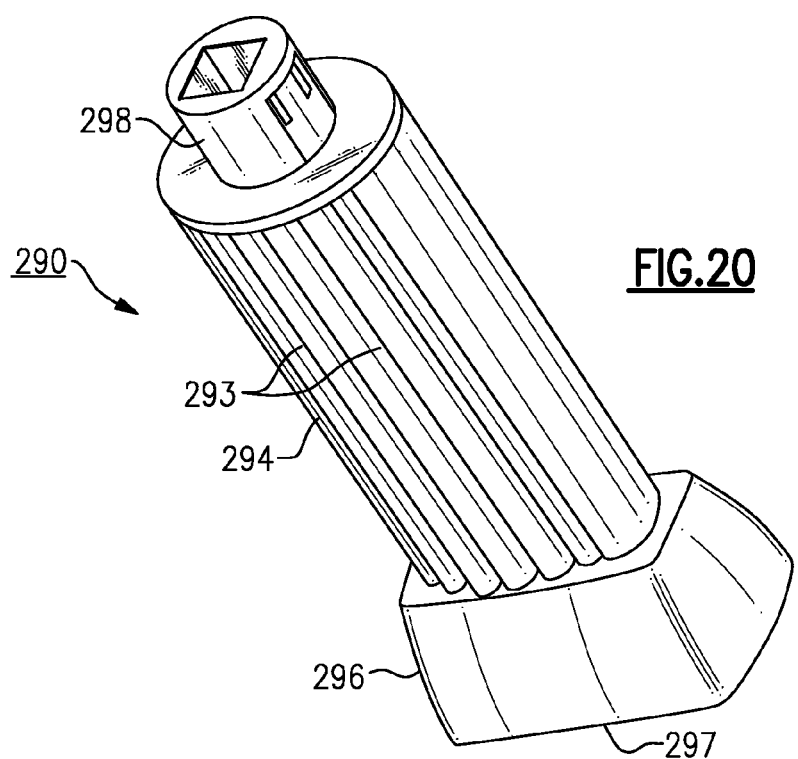
FIG. 20 is a top perspective view of a handle portion made in accordance with yet another embodiment.

Alternative handle portion designs 280, 290 are representatively illustrated in FIGS. 19 and 20. Each of these designs commonly include an upper coupling section 284, 294, a lower receiving section 286, 296 having an open end 287, 297 and a mating end 288, 298. As in the preceding, a portable illuminator 20, FIG. 2, can be releasably received within the open end 287, 297 of either handle portion 280, 290, the latter portion being attached by way of the mating end 288, 298, as shown according to FIG. 6, to the diagnostic instrument 200. In these versions, a set of heat dissipative ribs 283, 293 are provided on the exterior of each handle portion 280, 290. It will be readily apparent that other variations and modifications are possible for each of the handle portion and the portable illuminator and that the presently described versions are merely exemplary. For example and as previously noted, the handle portion can be made integral with the remainder of an instrument, as shown in FIG. 28, to further illustrate possible variations that are contemplated herein.

Figure 21:
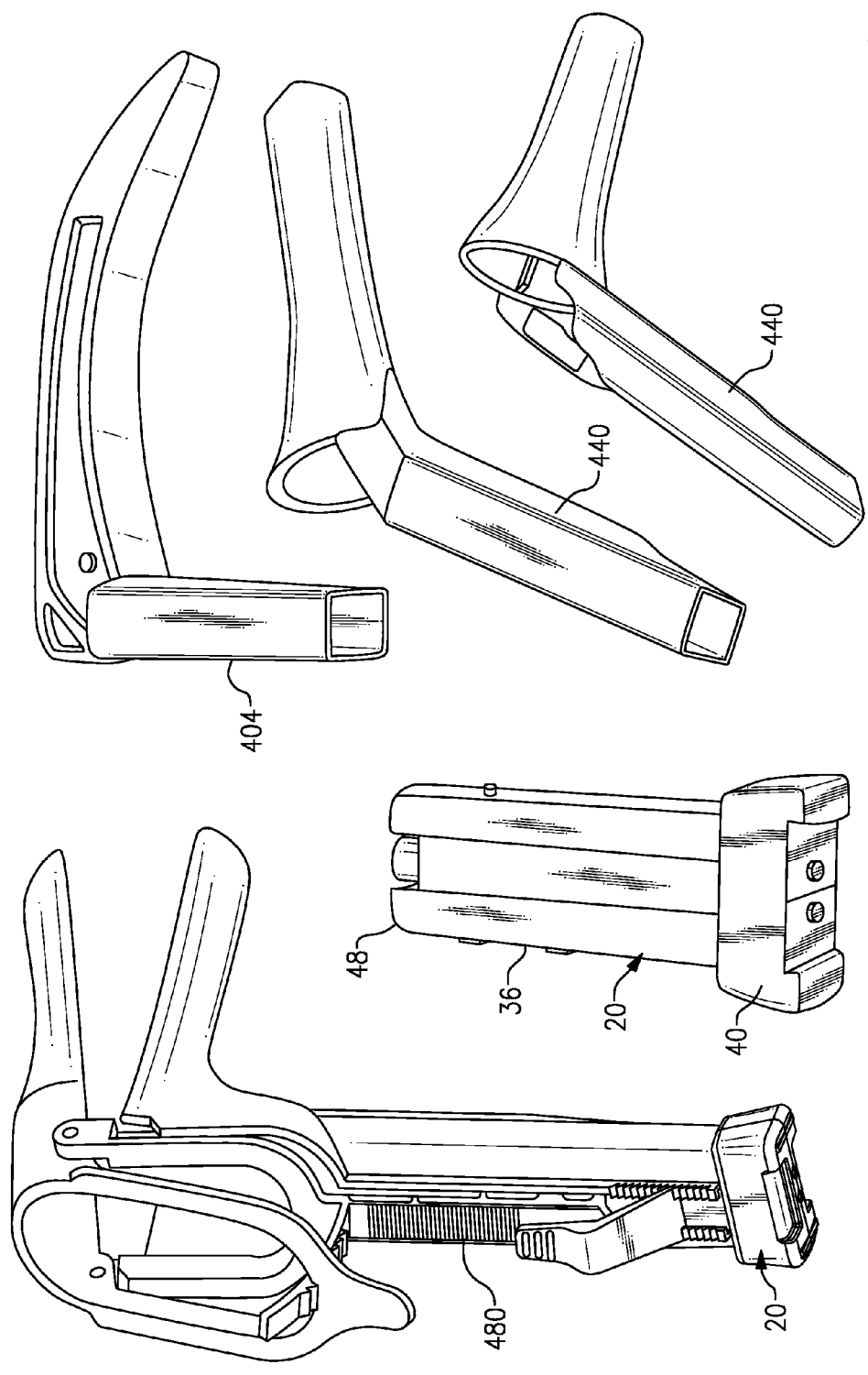
FIG. 21 illustrates a group of various medical diagnostic instruments each having handle portions made in accordance with embodiments of this application and configured to retain the portable illuminator of FIGS. 2-5.

The herein described design enables various diagnostic instruments to be configured, thereby enabling a portable illuminator to be commonly used therewith without modification. One such group of instruments is depicted in FIG. 21 including a laryngoscope 404, a set of anoscopes 440 (a standard anoscope and an operating anoscope being shown), and a vaginal speculum 480, each of which can be commonly or similarly configured to receive a portable illuminator 20, FIG. 2, or in conjunction with a disposable handle portion, such as the handle portion 280 previously depicted in FIG. 19, by way of example. The depicted vaginal speculum 480 has been previously described in PCT/US2006/012116 and is shown herein to further illustrate the overall versatility that can be created for a family of instruments configured according to the present invention. Each of the above instruments commonly includes a handle portion having a receiving cavity that is sized to substantially enclose the illuminator.

Figure 22:
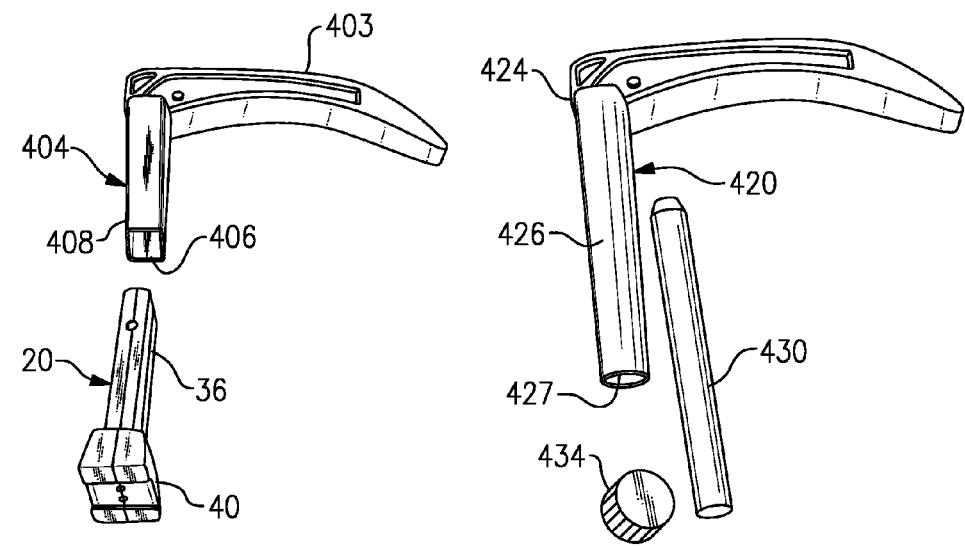
FIG. 22 illustrates a medical diagnostic instrument from the group shown in FIG. 21 in which a prior art instrument is compared to a medical diagnostic instrument having a handle portion made in accordance with an embodiment of the present invention.

Referring to FIG. 22, a prior art laryngoscope 420, depicted on the right hand side of this figure, is contrasted with the laryngoscope 404 shown in FIG. 21. The prior art laryngoscope 420 is defined by a body 424, which includes an integrated elongated handle 426 with an open end 427 that requires the insertion of a cartridge 430. The cartridge 430 is an electrically conductive (e.g., steel) cylindrical member that retains a set of stacked batteries (not shown), as well as a halogen light source (not shown), the cartridge being retained within the handle 426 by means of a cap 434 that is attached to the open end 427 of the handle.

Figure 22A:
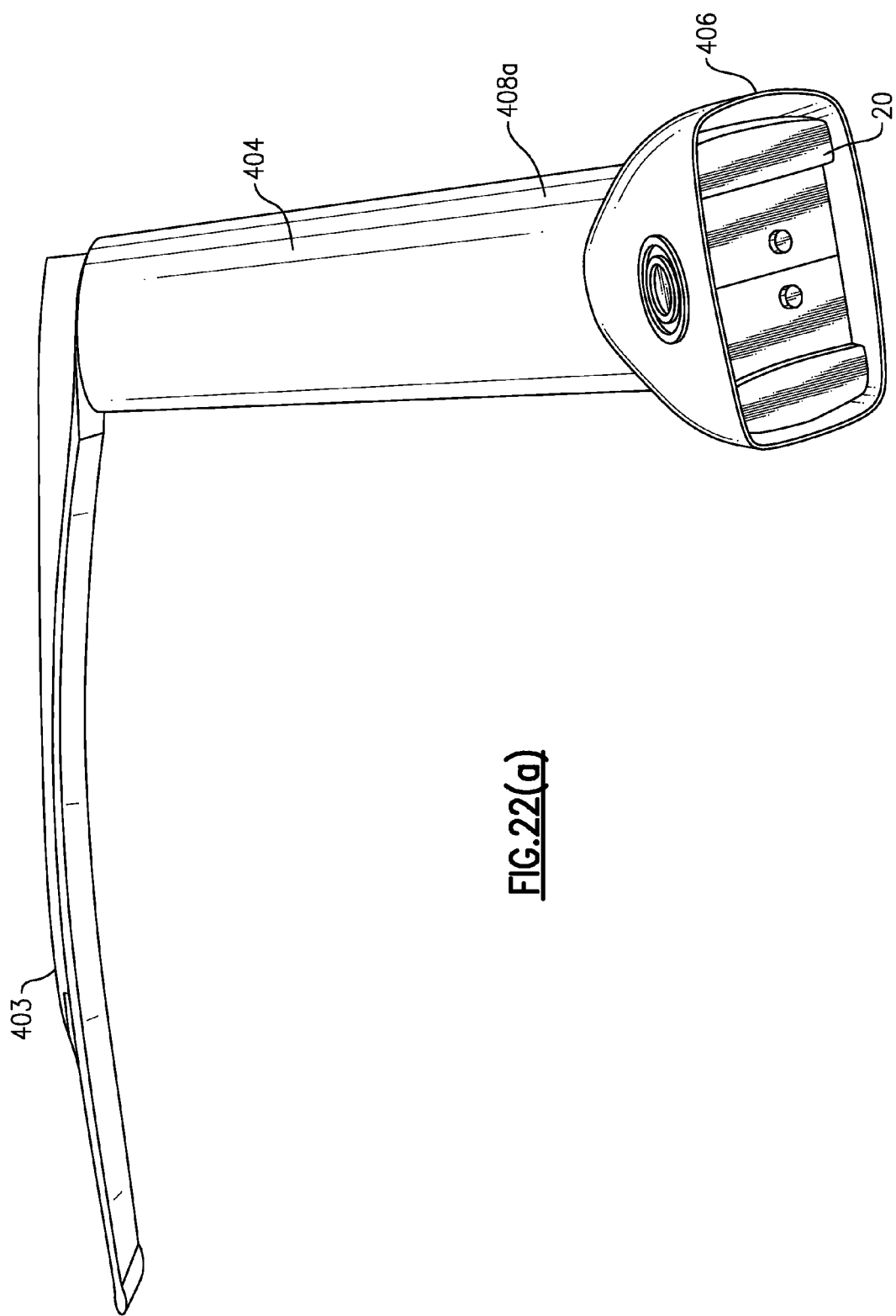
FIG. 22(a) depicts an assembled view of a laryngnoscope similar to that shown in the group of instruments shown in FIG. 22.

The laryngoscope 404 is defined by a plastic body 405 that includes an integrated handle portion 408 according to this exemplary embodiment, the handle portion having an open-ended elongated receiving cavity 406 which is sized to substantially fit the upper housing section of a portable illuminator 20, FIG. 2. Variations are possible, for example, an assembled version of the preceding is shown in FIG. 22(a) of a similarly constructed laryngoscope 404A having an elongated handle portion 408A with a receiving cavity that is configured to fully enclose the portable illuminator 20 as opposed to the instrument shown in FIG. 22, which merely retains the upper housing portion 36 thereof.

Figure 23:
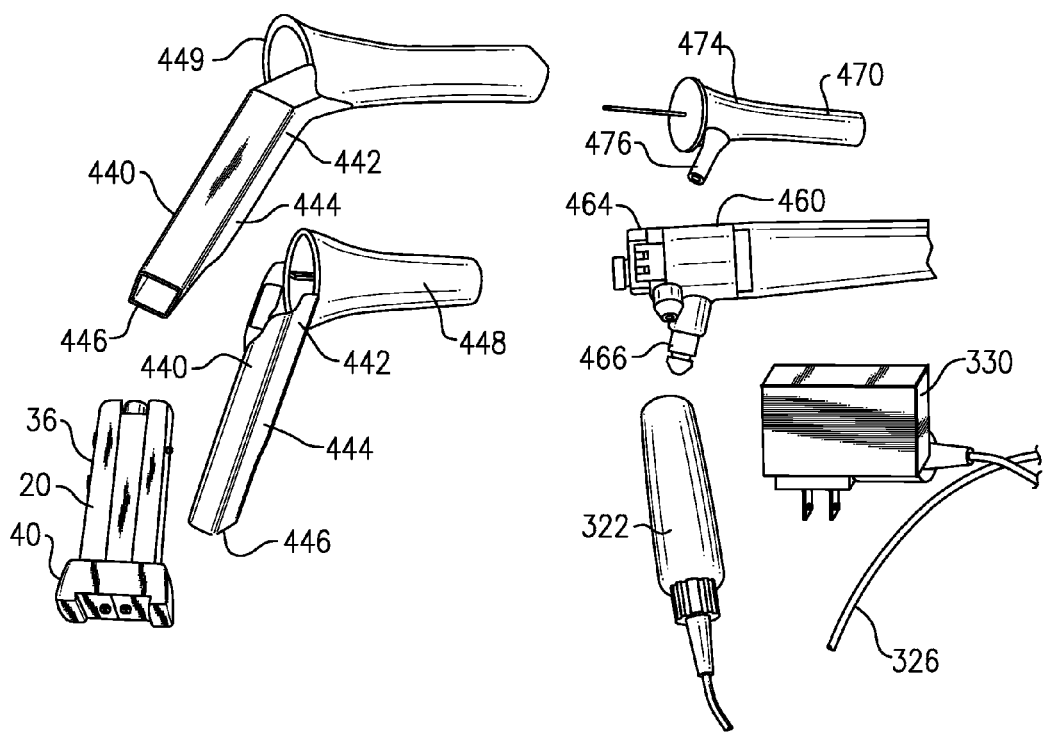
FIG. 23 illustrates another of the diagnostic instruments from the group shown in FIG. 21 in accordance with the prior art as compared to diagnostic instruments, each having a handle portion made in accordance with an embodiment of the present invention.

Similarly and referring to FIG. 23, prior art anoscopes 460, 470 are contrasted with the set of anoscopes 440 depicted in FIG. 21. According to the prior art versions 460, 470 and as previously discussed relative to FIG. 1, a tethered connection via cord 326 is required between a mating handle portion 322 and a transformer 320 to enable electrical power to be provided from a non-compact AC power supply (not shown) wherein the handle portion includes a light source (not shown) such as at least one incandescent bulb. Each of the anoscopes 460, 470 include different instrument heads, 464, 474, but include a common or similar engagement feature to enable the handle portion 308 to be attached in a releasable manner to permit optical coupling and illumination, as provided by the coupled handle portion 308, for patient examination. More specifically, the handle portion 308 shown can mate with an engagement end 466, 476 of the instruments 460, 470.

By way of contrast, the anoscopes 440 in accordance with the present embodiment are formed with an integrated handle portion 444 that includes an elongated open-ended receiving cavity 446 sized to at least partially receive the portable illuminator 20, FIG. 21. The instrument heads 448, 449 are also formed as part of the integrated body and are designed in order to perform the functions of their prior art counterparts. The presently described anoscopes 440 are made from a clear acrylic or similar material and are designed to be disposable, wherein the upper housing portion 36 of the portable illuminator 20 is contained within the elongated receiving cavity 446 of either anoscope 440, and coupled such that light is properly directed to the instrument head portion 448, 449 of the body 442 and to the patient to enable examination.

Figure 24:
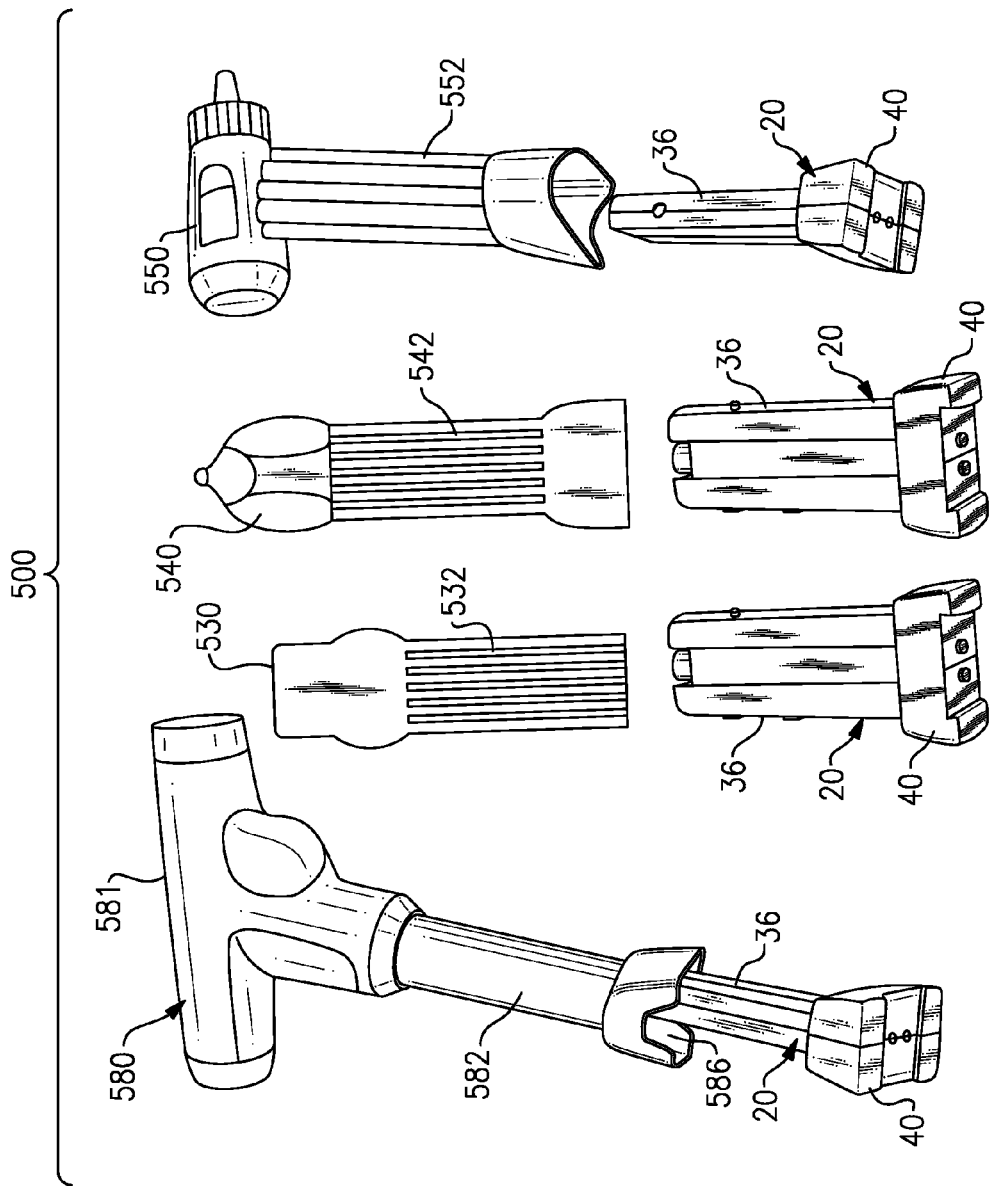
FIG. 24 illustrates another group of various medical diagnostic instruments made in accordance with embodiments of this application and configured to retain a portable illuminator.
Figure 24A:
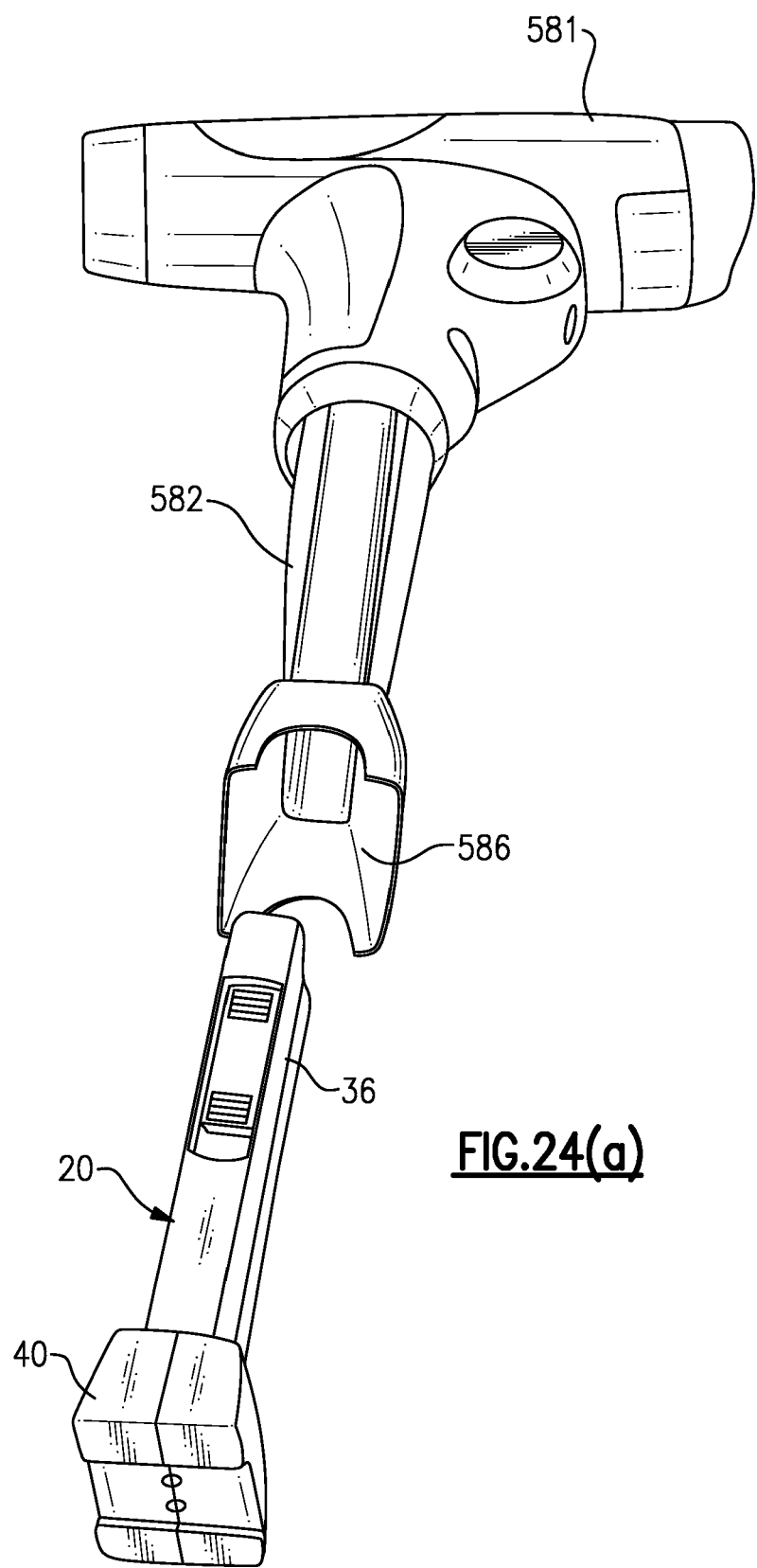
FIG. 24(a) illustrates a partially exploded view of an ophthalmoscope of FIG. 24 having a handle portion that is configured to receive a portable illuminator.

FIG. 24 illustrates another group 500 of hand-held medical diagnostic instruments that can be configured to accept a portable illuminator 20, this group including various ophthalmoscopes and otoscopic devices. As in the preceding, each instrument comprising this group 500 is suitably configured to accept a portable illuminator 20 having a contained power source/illumination source, but essentially in which a single illuminator can be easily used interchangeably with each instrument shown. As such, white LED technology can be easily translated into each instrument 500 for facilitating and improving overall examination time and procedure.

Figure 25:
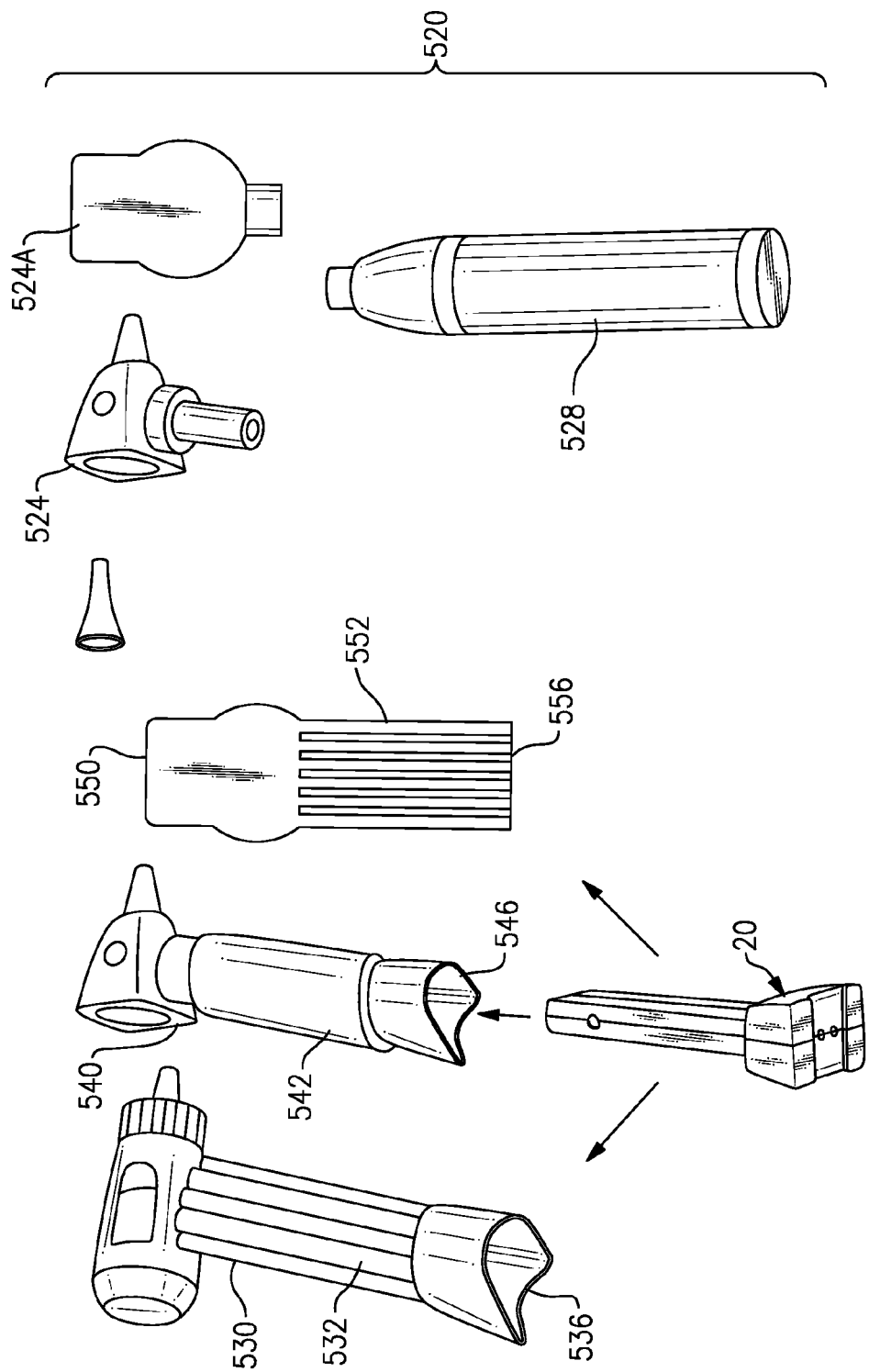
FIG. 25 illustrates a pair of medical diagnostic instruments (ophthalmoscope and otoscope) in accordance with the prior art as compared to various embodiments made in accordance with the present invention.
Figure 25A:
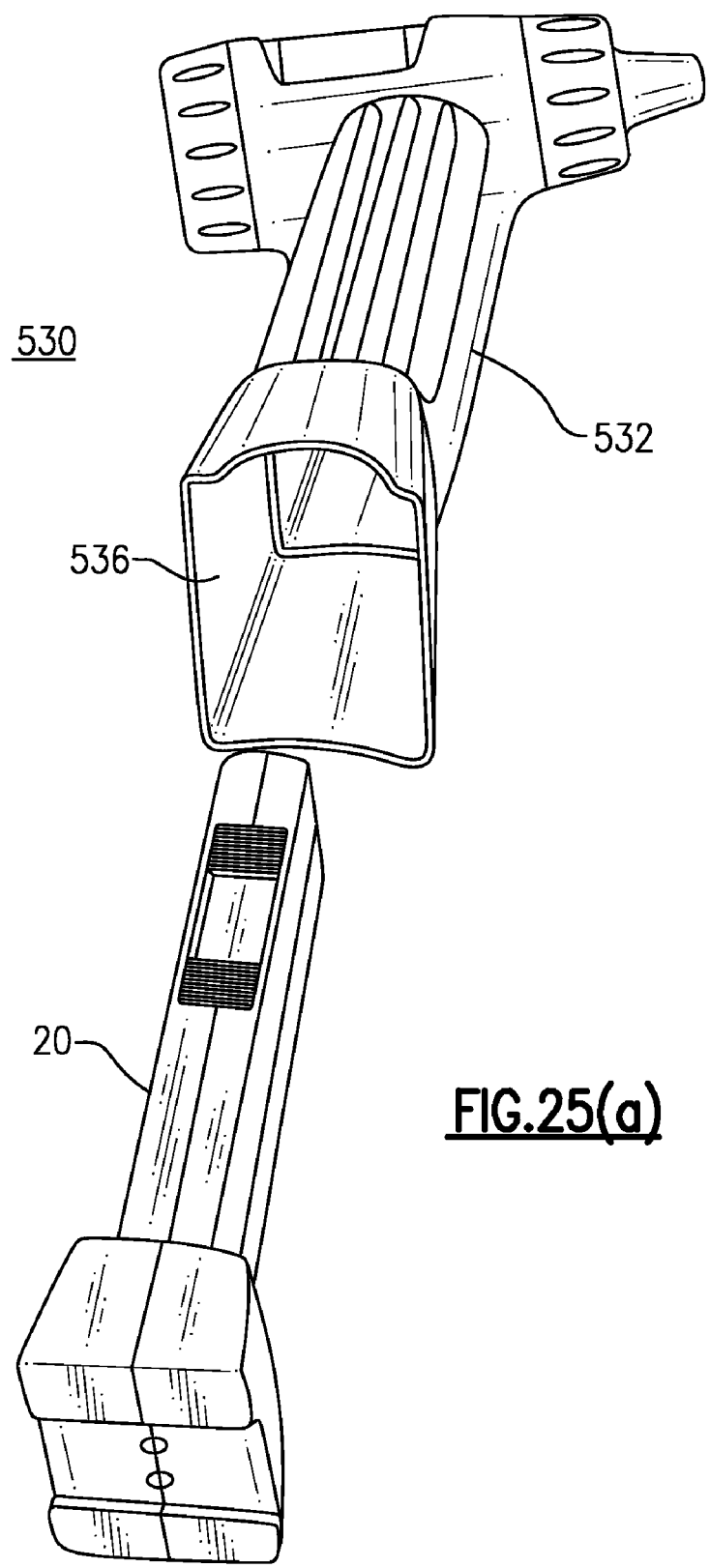
FIG. 25(a) is a partially exploded view of an otoscope of FIGS. 24 and 25 having a handle portion configured to receive a portable illuminator.
Figure 26:
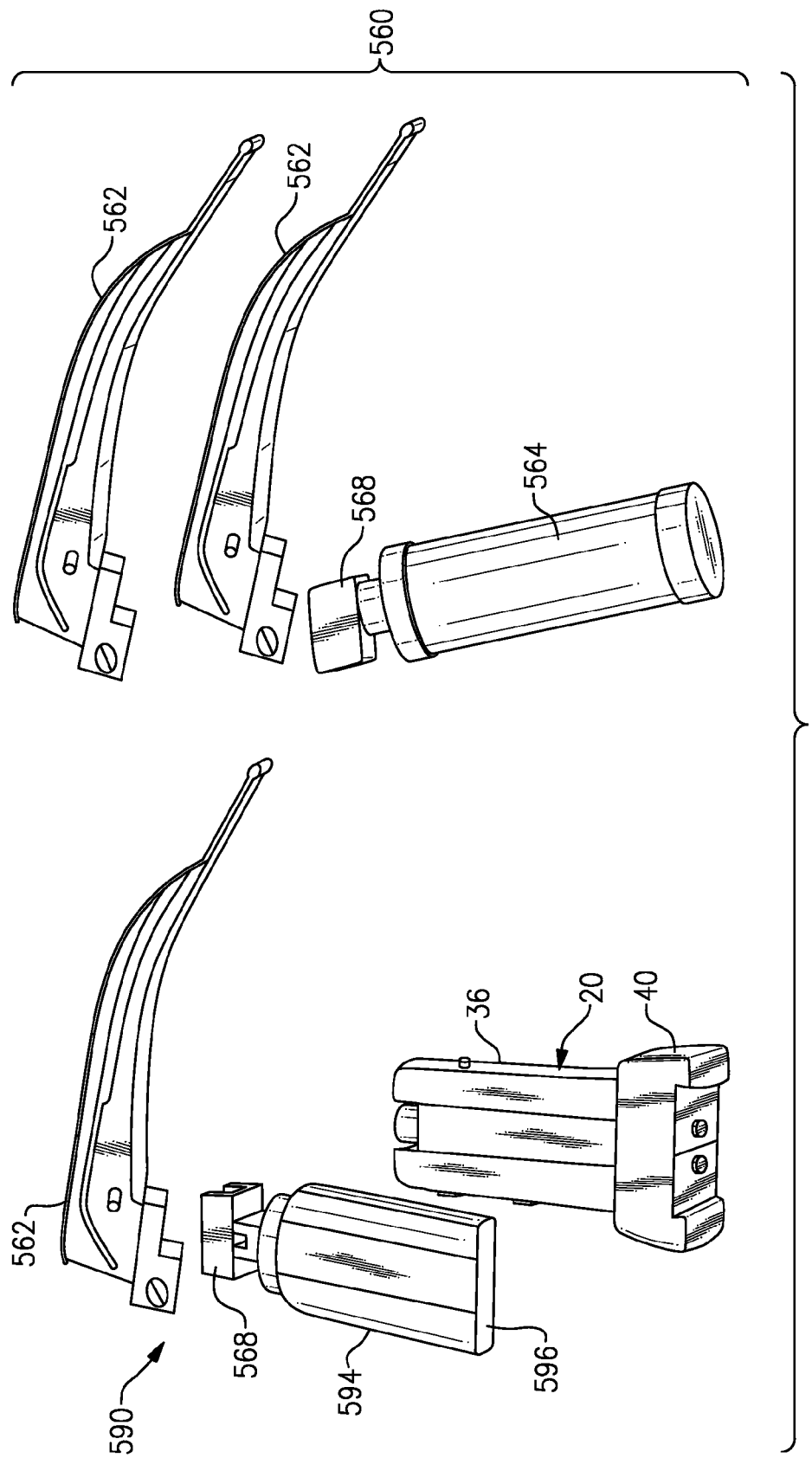
FIG. 26 illustrates another medical diagnostic instrument in accordance with the prior art as compared to an instrument which is made in accordance with another embodiment.

Referring to FIG. 25, an otoscope and opthalmoscope shown as group 520 according to the prior art are contrasted with various instrument designs 500 that are shown in FIG. 24. In the prior art versions, an otoscopic instrument head 524 or an opthalmoscopic instrument head 524A is attached by means of a bayonet-like engagement as described by U.S. Pat. No. 5,733,029 incorporated by reference herein, with the top of the handle portion 528 to initiate both mechanical and electrical connection. The handle portion 528 retains a halogen light source (not shown), as well as a set of batteries (not shown). In this prior art version, either the otoscopic instrument head 524 or the opthalmoscopic instrument head 524A can be commonly or interchangeably attached to the top of a single handle portion 528. While some versatility is demonstrated herein, this versatility is somewhat limited. This limitation is further shown, by way of example, in FIG. 26 in which reusable prior art laryngoscopes 560 require the use of an attached handle portion 564, but in which the attachment of the handle portion and the design thereof is quite different than that of the instrument group 520 in order to permit blades 562, 562A to be attached to the top of the handle portion. Put another way, the light and power sources of the prior art otoscope or opthalmoscope 520 cannot be used with the prior art laryngoscope 560.

On the other hand, the otoscopic versions 530, 540 and opthalmoscopic version 550 in accordance with the embodiments shown in FIGS. 24, 25 each commonly include a handle portion 532, 542, 552 that is formed with an elongated open-ended cavity 536, 546, 556 that can substantially receive a portable illuminator 20, whether partially as in the case of handle 532 or substantially the entirety of the illuminator as defined by handle portions 542, 552. In these versions, a bayonet connection between the instrument head and handle portion is no longer required. The instrument 530 is shown in greater detail in FIG. 25(*a*).

An alternative version is shown in FIG. 24 and FIG. 24(*a*) for another ophthalmoscope 580 having an instrument head 581 and handle portion 582. As in the preceding, the handle portion 582 is defined by an open bottom end extending to an elongated receiving cavity 586 that is sized and configured to substantially receive a portable illuminator 20. Moreover, the assembly of the illuminator 20 within the cavity 586 optically couples the light source (not shown) of the illuminator 20 with the instrument head 581 to permit emitted light to be properly directed for examination. The cavity of this version as well as any of the preceding versions can include features, such as those previously described with regard to FIGS. 7-18, is also configured to enable automatic energization of the contained light source of the illuminator 20 after the illuminator is properly inserted into the receiving cavity (as well as automatic deenergization when removed) as well as retention and release features, such as those previously described.

Referring back to FIG. 26, a laryngoscope 590 as contrasted with the previously referred to prior art instrument version 560. The laryngoscope 590 according to this embodiment is defined by a body 594 made from plastic or other suitable material, the body having a lower open end that, like the preceding, extends into an elongated receiving cavity 596 that is sized to minimally receive the upper housing portion 36 of a portable illuminator 20. In this design, the top of the handle portion 594 includes an attachment mechanism 568 enabling the mechanical attachment of the prior art device 560 between the blade 562 and the top of the handle portion 594 to be accomplished in the same manner as that of the instrument 560, but in which attachment of the compact illuminator 20 via the receiving cavity 596 provides optical coupling to a fiber optic (not shown) disposed within the blade 562.

Figure 27:
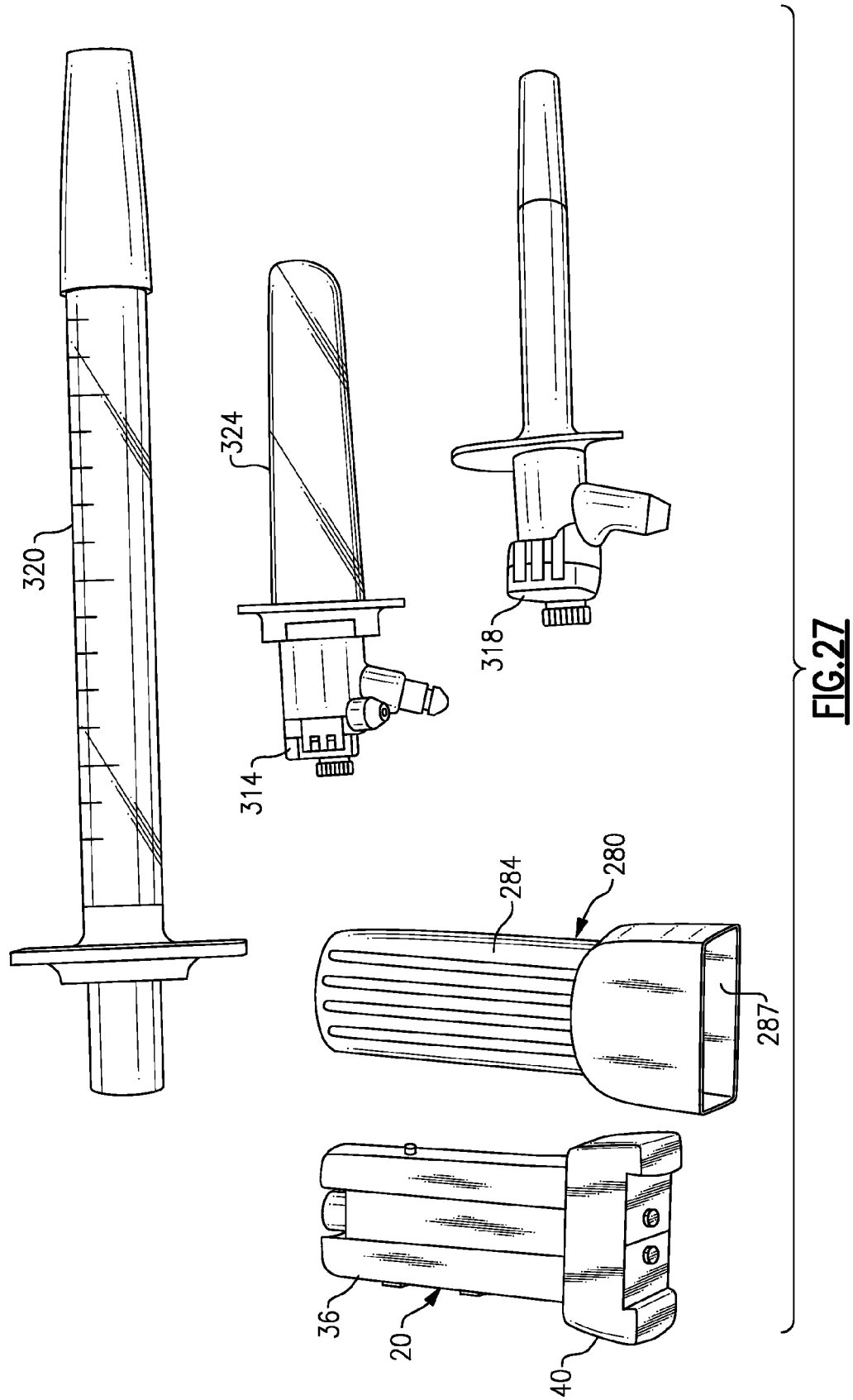
FIG. 27 depicts an assembly including the handle portion of FIG. 19 as used with sigmoidoscopes and anoscopes.

FIG. 27 illustrates the previously described handle portion 280 as used with the instrument group 300 of FIG. 1, including a sigmoidoscope and anoscope. As in the preceding, this handle portion 280 is defined by an open-ended receiving cavity 287 sized to substantially fit a portable illuminator 20 in its entirety. The handle portion 280 is preferably molded from a plastic material and includes an upper coupling portion 284 that includes a mating end engageable with the instrument head of the sigmoidoscope, wherein two types are illustrated, each commonly having an instrument head with various obturators attached to distal ends of the instrument heads.

Finally, FIG. 28 illustrates an alternative version of a handle portion that includes an eyepiece portion of a medical instrument 600, such as a sigmoidoscope. Like the preceding versions, the handle portion 604 of the instrument 600 includes an open-ended elongated cavity 608 to permit the retention of a portable illuminator 20 and to align the contained light source 28 (shown in phantom) of the illuminator optically with the remainder of the instrument. In this instance, the output of the contained light source 28 is directed to the proximal end 612 of a fiber optic 616 that is disposed in an upper coupling section 620 of the handle portion 604. The handle portion 604 is then attached by securing the distal end 628 of the upper coupling portion 620 to the proximal end 630 of an obturator 624, partially shown in FIG. 28, wherein the upper coupling portion further includes an eyepiece 640 sealingly engaged to the proximal end of the upper coupling portion. A port 644 is attached to the top of the upper coupling portion 620 of the handle portion 604, enabling pneumatic means (not shown) such as a bulb, to perform insufflation. As such, the features of the instrument head and handle portion 604 are integrated, but still permitting interchangeabilty across various instruments as concerning the portable illuminator 20.

In each of the foregoing examples and by enclosing at least a portion of the portable illuminator the possibility of cross contamination between patients is effectively minimized. The handle portion, whether disposable or reusable, provides a sheathing action with the exception of the open end of the receiving cavity into which the portable illuminator is introduced. As such, the illuminator does not require cleaning between examinations.

PARTS LIST FOR FIGS. 1-28

20 portable illuminator
21 primary axis, illuminator
24 housing or body section
25 lateral side
28 portable light source (LED)
32 portable power source (rechargeable battery)
34 front lens element
36 upper housing portion
39 top surface
40 lower base portion
42 nearest surface
44 substantially cylindrical region 47 spacings
48 shoulders
49 retaining structure
54 heat sink
56 lateral recess
58 retention pin
60 spring, pin
62 beveled end
66 slide switch
70 slotted area
74 tabs
78 spring, switch
84 dowel pin
86 leaf spring
92 printed circuit board
94 foam spacer
95 channels
96 flexible circuit assembly
98 tactile switch
100 extending electrical contacts
104 battery connector
108 low battery LED assembly
112 window
165 bottom surface
166 interface, illuminator
167 recessed portions
168 centerline
169 transverse rib
180 side walls
181 angled segment
182 angled segment
200 instrument
204 instrument head
208 handle portion
211 upper coupling section
212 mating upper end
213 lower retaining section
215 open end
217 elongated receiving cavity
219 arrows
220 hollow interior
221 flexure
223 engagement feature, instrument
224 top surface
228 center cavity
232 cylindrical portion
240 tubular lower portion
246 lower surface (lens)
250 upper portion
260 guide rails
264 center rail
268 ramped surface
280 handle portion
284 upper coupling section
286 lower receiving section
287 open ended receiving cavity
288 mating end
290 handle portion
294 upper coupling section
296 lower receiving section
297 open end
298 mating end
300 group—instruments
304 sigmoidoscope
312 anoscope
314 instrument head
318 instrument head
320 sigmoidoscope body
322 handle portion
324 sigmoidoscope body
326 cord
330 transformer
404 laryngoscope
405 body
406 elongated cavity
408 handle portion
420 laryngoscope, prior art
424 body
426 elongated handle
427 open end
430 cartridge
434 cap
440 anoscopes
442 body
444 handle portion
446 elongated receiving cavity
448 instrument head
449 instrument head
460 anoscope, prior art
464 instrument head
466 engagement feature
470 anoscope, prior art
474 instrument head
476 engagement end
480 vaginal speculum
500 group
520 otoscopes, prior art
524 instrument head
524A instrument head
528 handle portions
530 otoscope
532 handle portion
536 elongated receiving cavity
540 ophthalmoscope
542 handle portion
546 elongated receiving cavity
550 otoscope
552 handle portion
556 elongated receiving cavity
560 laryngoscopes, prior art
562 blade
564 handle portion
568 attachment mechanism
580 instrument
581 instrument head
582 body
586 elongated receiving cavity
590 instrument
594 body
596 elongated receiving cavity
600 instrument
604 handle portion
608 elongated cavity
612 proximal end, fiber optic
616 fiber optic
620 upper coupling section
624 obturator
628 distal end, handle portion
630 proximal end, obturator
640 eyepiece
644 port It will be appreciated that numerous variations and modifications will be apparent to those of sufficient skill in the field and that the exemplary versions disclosed herein are not intended to be exhaustive of the concepts as described by the following claims.

The invention claimed is:

1. A hand-held medical diagnostic instrument assembly, said assembly comprising:
   at least one hand held medical diagnostic instrument, said at least one instrument comprising an instrument head and a handle portion, said handle portion including an enclosed receiving cavity with an open proximal end; and
   an illuminator having a compact light source and a power supply each disposed within an interior of a housing, said illuminator being sized to fit substantially within the open proximal end of said enclosed receiving cavity in releasable fashion, said handle portion and said illuminator further including features for optically coupling the light source of a retained illuminator with said instrument head wherein said illuminator housing includes an upper cylindrical portion engageable with a tubular portion extending from the interior of the upper portion of said receiving cavity of said handle portion, said tubular portion of said handle portion further including at least one lens member aligned with said compact light source when said illuminator is attached in which said at least one lens member and said tubular portion are made from the same material and in which said at least one lens member is optically transmissive and said tubular portion is opaque.

2. An assembly as recited in claim 1, wherein said handle portion is releasably attached to said instrument head.

3. An assembly as recited in claim 2, wherein said handle portion is releasably attachable relative to said instrument head, said instrument head including an extending port and said handle portion including a socket engageable with said port.

4. An assembly as recited in claim 2, wherein said handle portion is disposable and said instrument head is reusable.

5. An assembly as recited in claim 4, wherein said handle portion is biodegradable.

6. An assembly as recited in claim 5, wherein said handle portion is made from a plastic material that is treated with an additive that renders the handle portion biodegradable.

7. An assembly as recited in claim 1, wherein said handle portion is integral to said instrument.

8. An assembly as recited in claim 1, wherein said receiving cavity includes at least one guide rail.

9. An assembly as recited in claim 1, wherein said tubular portion of said handle portion includes an integrally formed surface, said formed surface creating a seal between said illuminator and said instrument and in which said formed surface is said at least one lens member.

10. An assembly as recited in claim 1, wherein said handle portion includes at least one retaining feature for retaining said illuminator within said enclosed receiving cavity.

11. An assembly as recited in claim 1, wherein said handle portion further includes at least one feature for facilitating release of said illuminator from said handle portion.

12. An assembly as recited in claim 11, wherein at least a portion of said handle portion is flexibly deformable to facilitate release of said illuminator.

13. An assembly as recited in claim 12, wherein said open-ended receiving cavity includes at least one guide rail, said at least one guide rail including a ramped surface within said flexibly deformable portion of said handle portion for engaging said illuminator when deformed to facilitate release of said illuminator.

14. An assembly as recited in claim 1, including at least one heat dissipating rib in said receiving cavity.

15. An assembly as recited in claim 14, wherein said at least one heat dissipating rib also serves as guide rails in said enclosed receiving cavity for said illuminator.

16. An assembly as recited in claim 1, wherein said at least one hand-held medical diagnostic instrument is at least one of the group consisting of a sigmoidoscope, an anoscope, an ophthalmoscope and an otoscope, each of said instruments including a handle portion having an enclosed open-ended receiving cavity and tubular portion sized for releasably receiving and retaining said illuminator.

17. An assembly as recited in claim 1, wherein said handle portion is manufactured from a plastic material.

18. An assembly as recited in claim 1, wherein said illuminator is automatically energized when said illuminator is inserted in said receiving cavity, said illuminator including an external switch assembly engageable by a feature of said receiving cavity when said illuminator is inserted therein.

19. An assembly as recited in claim 18, wherein said illuminator is automatically caused to be deenergized when said illuminator is removed from said receiving cavity, said external switch assembly being biased to a non-energized position such that movement of said illuminator from said receiving cavity feature reverts said external switch assembly to the non-energized position.

20. A medical diagnostic instrument system, said instrument system comprising:
   a plurality of hand-held medical diagnostic instruments, each of said diagnostic instruments including a handle portion having an open-ended receiving cavity, said receiving cavity being entirely enclosed with the exception of an open proximal end and an instrument head, said plurality of instruments including at least two different instruments configured for examining different medical targets; and
   a portable illuminator interchangeably and releasably couplable with the open-ended receiving cavity of each of said plurality of hand-held diagnostic instruments, said illuminator being defined by a housing retaining a portable power supply and a compact light source, said compact light source being retained within a cylindrical upper portion of said illuminator housing, said handle portion including a hollow tubular portion sized to receive said upper cylindrical portion, said hollow tubular portion including a lens element therein that is aligned with the compact light source in which said lens element and said tubular portion are made from the same material and in which said lens element is optically transmissive and said tubular portion is opaque.

21. A system as recited in claim 20, wherein said housing of said illuminator is substantially enclosed within said receiving cavity of at least one said hand-held medical diagnostic instrument of said plurality of instruments.

22. A system as recited in claim 20, wherein said plurality of instruments include the group consisting of anoscopes, sigmoidoscopes, otoscopes, ophthalmoscopes, episcopes, vagiscopes, rhinoscopes and vaginal specula, each of said instruments including a handle portion having said receiving cavity and said tubular portion.

23. A system as recited in claim 20, wherein said handle portion is disposable.

24. A system as recited in claim 20, wherein said handle portion is integral to at least one of said plurality of diagnostic instruments.

25. A system as recited in claim 23, wherein said disposable handle portion of at least one diagnostic instrument of said plurality of instruments is releasably attached to said instrument head.

26. A system as recited in claim 20, wherein the receiving cavity of at least one handle portion substantially encloses said compact illuminator, said handle portion including an upper end that is sealed to prevent fluids from said instrument from entering said handle portion.

27. A system as recited in claim 20, wherein said at least one handle portion is made from a moldable material, said hollow tubular portion having a interface surface that provides a seal and includes a molded integral optical element serving as said lens element, said lens element being made from a thinned section of said moldable material to permit optical transmissivity with the remainder of said tubular portion being opaque.

28. A system as recited in claim 20, wherein said at least one handle portion is made from one of a plastic material having a biodegradable additive.

* * * * *